(12) United States Patent
Palanisamy et al.

(10) Patent No.: US 12,058,129 B2
(45) Date of Patent: Aug. 6, 2024

(54) POLICY-BASED GENOMIC DATA SHARING FOR SOFTWARE-AS-A-SERVICE TENANTS

(71) Applicant: Illumina, Inc., San Diego, CA (US)

(72) Inventors: Prabhu Palanisamy, Fremont, CA (US); Milan Karangutkar, Santa Clara, CA (US); Ryan Stinson, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 130 days.

(21) Appl. No.: 17/359,299

(22) Filed: Jun. 25, 2021

(65) Prior Publication Data

US 2021/0409400 A1 Dec. 30, 2021

Related U.S. Application Data

(60) Provisional application No. 63/045,736, filed on Jun. 29, 2020.

(51) Int. Cl.
*H04L 9/40* (2022.01)

(52) U.S. Cl.
CPC ...... *H04L 63/0876* (2013.01); *H04L 63/0236* (2013.01); *H04L 63/0807* (2013.01); *H04L 63/101* (2013.01); *H04L 63/102* (2013.01); *H04L 63/20* (2013.01)

(58) Field of Classification Search
None
See application file for complete search history.

(56) References Cited

U.S. PATENT DOCUMENTS

| 6,574,736 | B1 | 6/2003 | Andrews |
| 8,578,442 | B1 | 11/2013 | Banerjee |
| 8,850,546 | B1 | 9/2014 | Field et al. |
| 8,959,195 | B1 | 2/2015 | Niranjan et al. |
| 8,966,578 | B1 | 2/2015 | Belov et al. |
| 9,344,484 | B2 | 5/2016 | Ferris |
| 9,478,084 | B1 | 10/2016 | Robinson |

(Continued)

FOREIGN PATENT DOCUMENTS

| CN | 11625346 | 9/2020 |
| EP | 2746940 | 6/2014 |
| WO | WO 2013/176689 | 11/2013 |

OTHER PUBLICATIONS

Shiftehfar et al., "Towards a Flexible Fine-Grained Access Control System for Modern Cloud Applications," 2014 IEEE International Conference on Cloud Computing, IEEE Computer Society, pp. 966-967 (2014).

(Continued)

*Primary Examiner* — Khoi V Le

(74) *Attorney, Agent, or Firm* — Klarquist Sparkman, LLP

(57) ABSTRACT

Policy-based genomic digital data sharing facilitates a variety of sharing scenarios, including public access, tenant-to-tenant sharing, workgroup sharing, and access by external service providers. Genomic digital data can be published to the platform and controlled by access tokens that are generated based on access policies. The policies can support conditions that are evaluated at execution time and effectively place control of access to information in hands of the owning tenant. Sharing conditions can be easily specified to support various use cases, relieving administrators from excessive access control configuration.

20 Claims, 24 Drawing Sheets

(56) References Cited

U.S. PATENT DOCUMENTS

| | | |
|---|---|---|
| 9,602,508 B1 | 3/2017 | Mahaffey et al. |
| 9,774,586 B1 | 9/2017 | Roche et al. |
| 9,904,579 B2 | 2/2018 | Shear et al. |
| 9,940,266 B2 * | 4/2018 | Van Rooyen .......... G16H 10/60 |
| 10,044,723 B1 | 8/2018 | Fischer et al. |
| 10,207,184 B1 | 2/2019 | Leung et al. |
| 10,476,965 B1 | 11/2019 | Gray |
| 10,609,077 B1 | 3/2020 | Mehr |
| 10,628,244 B1 * | 4/2020 | Cseri .................. H04L 67/565 |
| 10,630,663 B1 | 4/2020 | Kasabwala et al. |
| 10,680,912 B1 | 6/2020 | Stelmar Netto et al. |
| 10,771,469 B1 | 9/2020 | Sarukkai et al. |
| 10,798,084 B1 | 10/2020 | Rose et al. |
| 10,798,100 B1 | 10/2020 | Chu et al. |
| 10,810,055 B1 | 10/2020 | Walker |
| 10,817,346 B1 | 10/2020 | Culp et al. |
| 10,911,407 B1 | 2/2021 | Warburton et al. |
| 10,911,564 B1 | 2/2021 | Sarukkai et al. |
| 10,962,939 B1 | 3/2021 | Das et al. |
| 10,977,218 B1 | 4/2021 | Umstot |
| 10,992,540 B1 | 4/2021 | Kandaswamy et al. |
| 10,999,355 B1 | 5/2021 | Chu et al. |
| 11,003,499 B1 | 5/2021 | Abretske et al. |
| 11,074,773 B1 | 7/2021 | Morris |
| 11,113,244 B1 | 9/2021 | Chen et al. |
| 11,153,325 B1 | 10/2021 | Igolnik et al. |
| 11,212,171 B1 | 12/2021 | Ozkan et al. |
| 11,228,573 B1 | 1/2022 | Rangasamy et al. |
| 11,310,238 B1 | 4/2022 | Vashisht et al. |
| 11,366,652 B1 | 6/2022 | Pressacco et al. |
| 11,956,228 B2 | 4/2024 | Yocom et al. |
| 2002/0165727 A1 | 11/2002 | Greene et al. |
| 2006/0062859 A1 | 3/2006 | Blum et al. |
| 2007/0271604 A1 * | 11/2007 | Webster .............. G06F 21/6245 726/10 |
| 2011/0251992 A1 | 10/2011 | Bethlehem et al. |
| 2011/0265147 A1 | 10/2011 | Liu |
| 2012/0017085 A1 | 1/2012 | Carter et al. |
| 2012/0204030 A1 | 8/2012 | Nossik et al. |
| 2012/0221696 A1 | 8/2012 | Ferris |
| 2012/0221845 A1 | 8/2012 | Ferris |
| 2012/0222084 A1 | 8/2012 | Beaty et al. |
| 2012/0278861 A1 | 11/2012 | Lu |
| 2012/0303814 A1 | 11/2012 | Ferris |
| 2012/0317648 A1 | 12/2012 | Brown et al. |
| 2013/0007845 A1 | 1/2013 | Chang et al. |
| 2013/0031224 A1 | 1/2013 | Nachtrab et al. |
| 2013/0061306 A1 | 3/2013 | Sinn |
| 2013/0073713 A1 | 3/2013 | Stelmar Netto |
| 2013/0160105 A1 | 6/2013 | Huang et al. |
| 2013/0232463 A1 | 9/2013 | Nagaraja et al. |
| 2013/0232480 A1 | 9/2013 | Winterfeldt et al. |
| 2013/0232497 A1 | 9/2013 | Jalagam et al. |
| 2013/0232498 A1 | 9/2013 | Mangtani et al. |
| 2013/0262556 A1 | 10/2013 | Xu et al. |
| 2014/0007189 A1 | 1/2014 | Huynh et al. |
| 2014/0026122 A1 | 1/2014 | Markande et al. |
| 2014/0053280 A1 | 2/2014 | Durazzo et al. |
| 2014/0075021 A1 | 3/2014 | Revanuru |
| 2014/0075427 A1 | 3/2014 | Pallamreddy et al. |
| 2014/0075520 A1 | 3/2014 | Subramanian et al. |
| 2014/0075565 A1 | 3/2014 | Srinivasan et al. |
| 2014/0082717 A1 | 3/2014 | Kang et al. |
| 2014/0089674 A1 | 3/2014 | Buehl |
| 2014/0096186 A1 | 4/2014 | Barton et al. |
| 2014/0108474 A1 | 4/2014 | David et al. |
| 2014/0122411 A1 | 5/2014 | Teichmann et al. |
| 2014/0123129 A1 | 5/2014 | Risbood et al. |
| 2014/0164776 A1 | 6/2014 | Hook et al. |
| 2014/0173112 A1 | 6/2014 | Seago et al. |
| 2014/0189124 A1 | 7/2014 | Banatwala et al. |
| 2014/0201524 A1 | 7/2014 | Dittrich |
| 2014/0223576 A1 | 8/2014 | Zhao |
| 2014/0373104 A1 | 12/2014 | Gaddam et al. |
| 2015/0052353 A1 | 2/2015 | Kang et al. |
| 2015/0106881 A1 | 4/2015 | Wharton et al. |
| 2015/0120900 A1 | 4/2015 | Sahoo et al. |
| 2015/0172321 A1 | 6/2015 | Kirti et al. |
| 2015/0188927 A1 | 7/2015 | Santhi et al. |
| 2015/0200958 A1 | 7/2015 | Muppidi et al. |
| 2015/0227697 A1 * | 8/2015 | Nelson .................. G16B 50/00 705/3 |
| 2015/0244710 A1 | 8/2015 | Koster et al. |
| 2015/0304231 A1 | 10/2015 | Gupte et al. |
| 2015/0372857 A1 | 12/2015 | Hasan et al. |
| 2016/0065616 A1 | 3/2016 | Srikanth et al. |
| 2016/0080501 A1 | 3/2016 | Freimuth et al. |
| 2016/0134619 A1 | 5/2016 | Mikheev et al. |
| 2016/0162701 A1 | 6/2016 | Rosenburg et al. |
| 2016/0255095 A1 | 9/2016 | Maes |
| 2016/0277411 A1 | 9/2016 | Dani et al. |
| 2016/0315768 A1 | 10/2016 | Fu et al. |
| 2017/0006032 A1 | 1/2017 | Simpson et al. |
| 2017/0006064 A1 | 1/2017 | Agarwal et al. |
| 2017/0018130 A1 | 1/2017 | Robinson |
| 2017/0032092 A1 | 2/2017 | Mink et al. |
| 2017/0046230 A1 | 2/2017 | Guzik |
| 2017/0076105 A1 | 3/2017 | Paulovicks et al. |
| 2017/0142124 A1 | 5/2017 | Mukhin et al. |
| 2017/0171164 A1 | 6/2017 | Alexander et al. |
| 2017/0171179 A1 | 6/2017 | Buendgen et al. |
| 2017/0171197 A1 | 6/2017 | Alexander et al. |
| 2017/0177613 A1 | 6/2017 | Sharma et al. |
| 2017/0187703 A1 | 6/2017 | Enrique Salpico |
| 2017/0201549 A1 | 7/2017 | Vincent et al. |
| 2017/0223117 A1 | 8/2017 | Messerli et al. |
| 2017/0228559 A1 | 8/2017 | Jackson |
| 2017/0279692 A1 | 9/2017 | Llagostera et al. |
| 2017/0329957 A1 * | 11/2017 | Vepa ...................... G06F 21/445 |
| 2017/0353457 A1 | 12/2017 | Steeves et al. |
| 2017/0357456 A1 | 12/2017 | DeFlippi et al. |
| 2017/0357798 A1 | 12/2017 | Khan et al. |
| 2017/0366525 A1 | 12/2017 | Takagi et al. |
| 2017/0372094 A1 | 12/2017 | Hore |
| 2018/0026985 A1 | 1/2018 | Pogrebinsky |
| 2018/0027006 A1 | 1/2018 | Zimmermann et al. |
| 2018/0027050 A1 | 1/2018 | Pogrebinsky et al. |
| 2018/0041483 A1 | 2/2018 | Smith et al. |
| 2018/0046823 A1 | 2/2018 | Durham et al. |
| 2018/0060894 A1 | 3/2018 | Beverdige et al. |
| 2018/0061243 A1 | 3/2018 | Shloosh |
| 2018/0077138 A1 | 3/2018 | Bansal et al. |
| 2018/0082073 A1 | 3/2018 | Trachy |
| 2018/0091306 A1 | 3/2018 | Antonopoulos et al. |
| 2018/0097809 A1 | 4/2018 | Chakrabarti et al. |
| 2018/0103039 A1 | 4/2018 | Thaler et al. |
| 2018/0114116 A1 | 4/2018 | Liang et al. |
| 2018/0121486 A1 | 5/2018 | Puvvada et al. |
| 2018/0123361 A1 | 5/2018 | Gray |
| 2018/0189661 A1 | 7/2018 | Tatourian et al. |
| 2018/0205618 A1 | 7/2018 | Weiner et al. |
| 2018/0212928 A1 | 7/2018 | Gerber et al. |
| 2018/0227185 A1 | 8/2018 | Turner et al. |
| 2018/0287864 A1 | 10/2018 | Hockett et al. |
| 2018/0288045 A1 | 10/2018 | Karunakaran et al. |
| 2018/0300557 A1 | 10/2018 | Rodenas et al. |
| 2018/0322946 A1 | 11/2018 | Ika et al. |
| 2018/0329744 A1 | 11/2018 | Shear et al. |
| 2018/0375886 A1 | 12/2018 | Kirti et al. |
| 2019/0058709 A1 | 2/2019 | Kempf et al. |
| 2019/0065679 A1 * | 2/2019 | Powers ................ H04L 63/083 |
| 2019/0066012 A1 | 2/2019 | Abell et al. |
| 2019/0087600 A1 | 3/2019 | Sion et al. |
| 2019/0098037 A1 | 3/2019 | Shenoy, Jr. et al. |
| 2019/0103968 A1 | 4/2019 | Srinivasan et al. |
| 2019/0180186 A1 | 6/2019 | Liang et al. |
| 2019/0238542 A1 | 8/2019 | Kilroy et al. |
| 2019/0253509 A1 | 8/2019 | Kumar et al. |
| 2019/0273761 A1 | 9/2019 | Srikanth et al. |
| 2019/0180187 A1 | 10/2019 | Rawai et al. |
| 2019/0306010 A1 | 10/2019 | Medam et al. |
| 2019/0318100 A1 | 10/2019 | Bhatia et al. |
| 2019/0319839 A1 | 10/2019 | Nozhchev et al. |
| 2019/0356661 A1 | 11/2019 | Hecht |

(56) References Cited

U.S. PATENT DOCUMENTS

| | | |
|---|---|---|
| 2019/0380020 A1 | 12/2019 | Pellegrini et al. |
| 2019/0394204 A1 | 12/2019 | Bansal et al. |
| 2020/0004589 A1 | 1/2020 | Geiger et al. |
| 2020/0007541 A1 | 1/2020 | Appiah et al. |
| 2020/0036599 A1 | 1/2020 | Savov et al. |
| 2020/0053089 A1 | 2/2020 | Singh |
| 2020/0099515 A1 | 3/2020 | Hopkins |
| 2020/0099685 A1 | 3/2020 | Wijaya et al. |
| 2020/0128047 A1 | 4/2020 | Biswas et al. |
| 2020/0159953 A1 | 5/2020 | Straw |
| 2020/0160985 A1 | 5/2020 | Kusuma et al. |
| 2020/0177591 A1 | 6/2020 | Pogrebinsky |
| 2020/0177621 A1 | 6/2020 | Boulton |
| 2020/0203966 A1 | 6/2020 | Gray |
| 2020/0228973 A1 | 7/2020 | Kasabwala et al. |
| 2020/0252205 A1 | 8/2020 | Padmanbhan |
| 2020/0274780 A1 | 8/2020 | Richardson |
| 2020/0278813 A1 | 9/2020 | Nilsson |
| 2020/0314191 A1 | 10/2020 | Madhavan et al. |
| 2020/0314623 A1 | 10/2020 | Pellegrini et al. |
| 2020/0344235 A1 | 10/2020 | Bhuiyan et al. |
| 2020/0358779 A1 | 11/2020 | Momchilov et al. |
| 2020/0359212 A1 | 11/2020 | Chen et al. |
| 2020/0374187 A1 | 11/2020 | Sako |
| 2021/0064262 A1 | 3/2021 | Myers et al. |
| 2021/0081439 A1 | 3/2021 | Glickman et al. |
| 2021/0092105 A1 | 3/2021 | Yu et al. |
| 2021/0099360 A1 | 4/2021 | Parsons et al. |
| 2021/0144225 A1 | 5/2021 | Grivogiannis |
| 2021/0216410 A1 | 7/2021 | Jin et al. |
| 2021/0224194 A1 | 7/2021 | Harar et al. |
| 2021/0266309 A1 | 8/2021 | Guggione et al. |
| 2021/0271777 A1 | 9/2021 | Netsch et al. |
| 2021/0288970 A1 | 9/2021 | Chawla et al. |
| 2021/0297417 A1 | 9/2021 | Pogrebinsky |
| 2021/0344485 A1 | 11/2021 | Levin et al. |
| 2021/0352045 A1 | 11/2021 | Kodavanty |
| 2021/0352138 A1 | 11/2021 | Kodavanty et al. |
| 2021/0392049 A1 | 12/2021 | Jeuk et al. |
| 2021/0397729 A1 | 12/2021 | McQuaid |
| 2021/0409409 A1 | 12/2021 | Palanisamy |
| 2022/0029994 A1 | 1/2022 | Choyi et al. |
| 2022/0107846 A1 | 4/2022 | Culp et al. |
| 2022/0114262 A1 | 4/2022 | Bhatia et al. |
| 2022/0166765 A1 | 5/2022 | Pattar et al. |
| 2022/0345483 A1 | 10/2022 | Shua |
| 2022/0413933 A1 | 12/2022 | Muthuganesan |
| 2023/0037542 A1 | 2/2023 | Revanuru |
| 2023/0239301 A1 | 7/2023 | Ivanov et al. |
| 2023/0247003 A1 | 8/2023 | Chanak et al. |
| 2023/0259994 A1 | 8/2023 | Raffel et al. |
| 2023/0281087 A1 | 9/2023 | Polevoy et al. |
| 2023/0291667 A1 | 9/2023 | Sivakumar et al. |
| 2023/0336536 A1 | 10/2023 | Maria et al. |
| 2023/0344698 A1 | 10/2023 | Sivakumar et al. |
| 2023/0344918 A1 | 10/2023 | Chibon et al. |
| 2024/0056388 A1 | 2/2024 | Chen et al. |

OTHER PUBLICATIONS

Su et al., "Cloud Access Control in Multi-Layer Cloud Networks," 2015 International Conference on Consumer Electronics—Taiwan, ICCE-TW, pp. 364-365 (2015).
International Search Report received in counterpart PCT Application No. PTC/US2021/039234, dated Sep. 22, 2021, 3 pages.
Written Opinion, received in counterpart PCT Application No. PTC/US2021/039234, dated Sep. 22, 2021, 5 pages.
Gholami et al., "A Security Framework for Population-Scale Genomics Analysis," 2015 International Conference on High Performance Computing & Simulation (HPCS), IEEE, Jul. 20, 2015 pp. 106-114, 9 pages.
Abbadi et al., "Secure Virtual Layer Management in Clouds," 2011 International Joint Conference of IEEE TrustCom-11/IEEE/ICESS-11/FCST-11, IEEE Computer Society, pp. 99-110 (2011).
Kappes et al., "Multitenant Access Control for Cloud-Aware Distributed Filesystems, IEEE Transactions on Dependable and Secure Computing," vol. 16, No. 6, pp. 1070-1085 (2017).
"IBM and Illumina Partner to Standardize Genomic Data Interpretation," BioSpace, Jan. 9, 2017, 4 pages.
"BaseSpace Sequence Hub," Illumina.com, visited Oct. 7, 2019, 5 pages.
"BaseSpace Clarity LIMS Security and Privacy," Illumina.com, Jan. 16, 2017, 8 pages.
"White Paper on the objectives and benefits of the MPEG-G standard," GenomSys.com, visited Aug. 2, 2019, 15 pages.
PetaSuite Protect, PetaGene, www.petagene.com, visited Oct. 7, 2019, 1 page.
"Overview," PetaGene, www. Petagene.com, visited Oct. 7, 2019, 3 pages.
"Multenancy," Google Cloud, cloud.google.com, visited Oct. 9, 2019, 4 pages.
"Enabling responsible genomic data sharing for the benefit of human heath," Global Alliance for Genomics & Health, GA4GH. com, Nov. 30, 2019, 5 pages.
"DUO—the Data Use Ontology," Global Alliance for Genomics & Health, github.com/EBISPOT/DUO, Nov. 30, 2019, 9 pages.
"What is a Phenopacket?" phenopackets-schema.readthedocs.io, Nov. 30, 2019, 2 pages.
"Genomic Data Toolkit," Global Alliance for Genomics & Health, www.ga4gh.org/genomic-data-toolkit/, Nov. 30, 2019, 11 pages.
"Framework for Responsible Sharing of Genomic and Health-Related Data," Global Alliance for Genomics & Health, www.ga4gh.org/genomic-data-toolkit, Sep. 2014, 9 pages.
"Security Technology Infrastructure," Global Alliance for Genomics & Health, Version 3.0, Aug. 15, 2019, 1 page.
Field et al., "The Genomics Standards Consortium," PLoS Biol. Jun. 2011; 9(6): e1001088, Jun. 21, 2011, 7 pages.
"Lightweight Directory Access Protocol," *Wikipedia*, accessed Nov. 30, 2019, 13 pages.
Zhao, "IAM Policies and Bucket Policies and ACLs! Oh My! (Controlling Access to S3 Resources)," aws.amazon.com/blogs, Nov. 19, 2013, 7 pages.
"Illumina Dragen™ Bio-IT Platform," Document 970-2018-002-B Illumina, Inc., on or before Dec. 2018, 5 pages.
"Policy-Based Access Control (PBAC)," csrc.glossary, csrc.nist.gov, visited Dec. 18, 2019, 2 pages.
International Search Report received in PCT Application No. PCT/US2021/039237, dated Sep. 28, 2021, 3 pages.
Written Opinion received in PCT Application No. PCT/US2021/039237, dated Sep. 28, 2021, 6 pages.
Gonzalez et al., "A Framework for Authentication and Authorization Credentials in Cloud Computing," 2013 12 IEEE International Conference on Trust, Security and Privacy in Computing and Communications, IEEE Computer Society, pp. 509-516, 2013.
Dewangan et al., Credential and Security Issues of Cloud Service Models, 2016 2nd International Conference on Next Generation Computing Technologies (NGCT-2016) pp. 888-892 (2016).
Messerges et al., "Securing Derived Credentials on a Mobile Device," IEEE Computer Society, pp. 249-254.
Pape et al., "Selecting a Secure Cloud Provider-An Empirical Study and MultiCriteria Approach," MDPI, Information 2020, 11, 261, pp. 1-27, 27 p. (2020).
Cidres et al., "Cloud Calculator: A cloud assessment tool for Public Administration," ACM, pp. 130-137, 8 p. (2020).
Zhong et al., "Construction of a Trusted SaaS Platform," 2010 Firth IEEE International Symposium on Service Oriented System Engineering, IEEE Computer Society, pp. 244-251 (2010).
Rashmi et al., Securing Software as a Service Model of Cloud Computing: Issues and Solutions, International Journal on Cloud Computing: Services and Architecture (IJCCSA), vol. 3, No. 4, pp. 1-11 (2013).

* cited by examiner

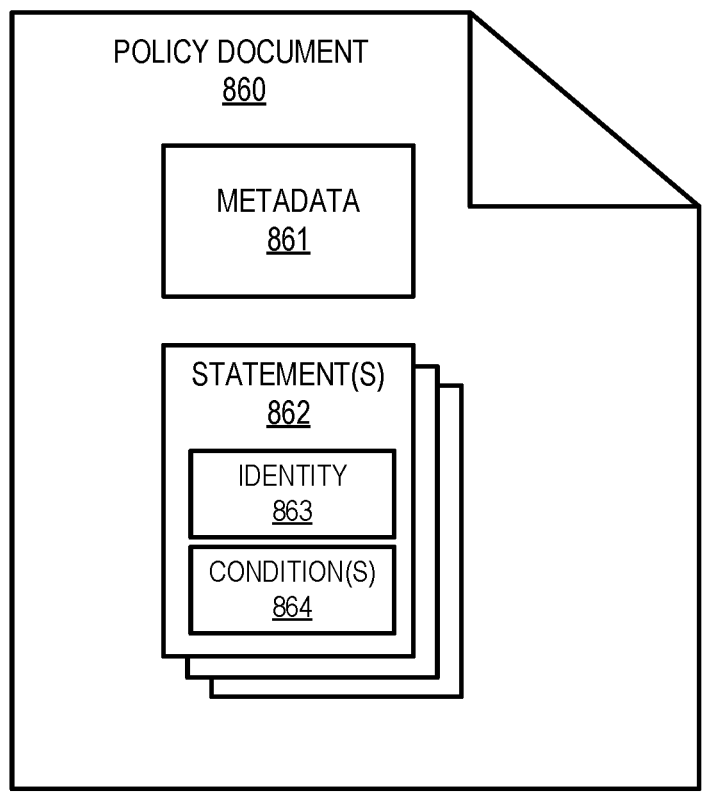
FIG. 8

POLICY-BASED GENOMIC DATA SHARING FOR SOFTWARE-AS-A-SERVICE TENANTS

CROSS REFERENCE TO RELATED APPLICATIONS

This application claims the benefit of U.S. Provisional Application No. 63/045,736, filed on Jun. 29, 2020, which is hereby incorporated herein by reference.

FIELD

The field generally relates to sharing data among software-as-a-service (SAAS) tenants.

BACKGROUND

The study of genomic data can involve complex analysis by a variety of parties with differing expertise collaborating over time. Research typically starts with genomic data that may come from a variety of sources. The data can then be analyzed using a wide variety of techniques. Today's research projects can involve parties spread throughout the world who share data and/or collaborate on data analysis. While strides have been made in the field, and international standards for sharing genomic data have been developed, significant challenges to sharing genomic data still remain.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a method comprises, in a computing system comprising a plurality of tenants seeking access to genomic digital data resources provided by one or more genomic data services in a software-as-a-service platform that orchestrates access to the genomic digital data resources via policy-based access control, receiving a policy-based access control definition for a first of the tenants for a given genomic digital data resource; receiving a request for access to the given genomic digital data resource from a second of the tenants seeking access to the given genomic digital data resource; and, for the second of the tenants, granting access to the given genomic digital data resource based on the policy-based access control definition.

In another embodiment, A multi-tenant, cloud-based system comprises one or more processors; memory coupled to the one or more processors; a policy store comprising a policy-based access control definition received for a first tenant and comprising a role identifier; a genomic digital data resource linked to the role identifier; wherein the memory comprises computer-executable instructions causing the one or more processors to perform operations comprising: receiving a request for access to the genomic digital data resource from a second tenant seeking access to the genomic digital data resource; and for the second tenant, granting access to the genomic digital data resource according to the policy-based access control definition evaluated at a time of the request for access.

In another embodiment, one or more computer-readable media comprise computer-executable instructions capable of causing a computing system to receive a publishing request for a first tenant to provide access to genomic digital data, wherein access to the genomic digital data is controlled by a role identifier linked to a policy document, wherein the policy document comprises one or more conditions; computer-executable instructions capable of causing a computing system to receive a request from a second tenant for access to the genomic digital data to which access is controlled by the role identifier linked to the policy document, wherein the request comprises one or more attributes; computer-executable instructions capable of causing the computing system to access the policy document responsive to the request from the second tenant for access; and computer-executable instructions capable of causing the computing system to generate an access token based on the one or more attributes and the one or more conditions, wherein the role identifier is included in the access token responsive to determining that the one or more conditions are fulfilled by the one or more attributes. and the access token authorizes access to the genomic digital data via the role identifier.

BRIEF DESCRIPTION OF THE DRAWINGS

FIG. 8 is a block diagram of an example policy document.

DETAILED DESCRIPTION

Example 1—Overview

The ever-growing availability of genomic data presents new opportunities for research and analysis. Today's sequencing platforms can generate a wide variety of sequenced output, including whole-genome sequencing (WGS). Also, various organizations such as the Global Alliance for Genomics & Health have developed standards for sharing genomic data. However, in practice, today's genomic information ecosystem can appear fractured at times. Data may be segregated or segmented into silos due to a variety of considerations, including technical, security, legal, and financial reasons. And, even when data is publicly available, it may not be fully integrated in such a way that it is immediately useful.

One large hurdle is sharing information among parties. A fully open platform that allows all participants to share every piece of data of every other participant is not realistic or desirable. However, a policy-based approach to sharing genomic digital data among software-as-a-service tenants can allow parties to share data in a controlled way that encourages collaboration between parties. Public data can be included, and external service providers can also participate. Access control can be automated and more easily controlled without having to manually engage in lengthy, complex security administration.

As a result, a cloud-based platform can serve as a virtual space in which parties from a wide variety of backgrounds and institutions can collaborate, sharing data, knowledge, tools, workflows, and applications to converge on innovative insights and arrive at new solutions.

Released from technical limitations, data can migrate to where it is needed, and a more cooperative ecosystem can result. Because the technologies apply to genomic digital data generally, they can be applied across a large number of use cases involving genomic digital data storage, retrieval, and analysis.

Example 2—Example System Implementing Policy-Based Genomic Digital Data Sharing

Figure 1:
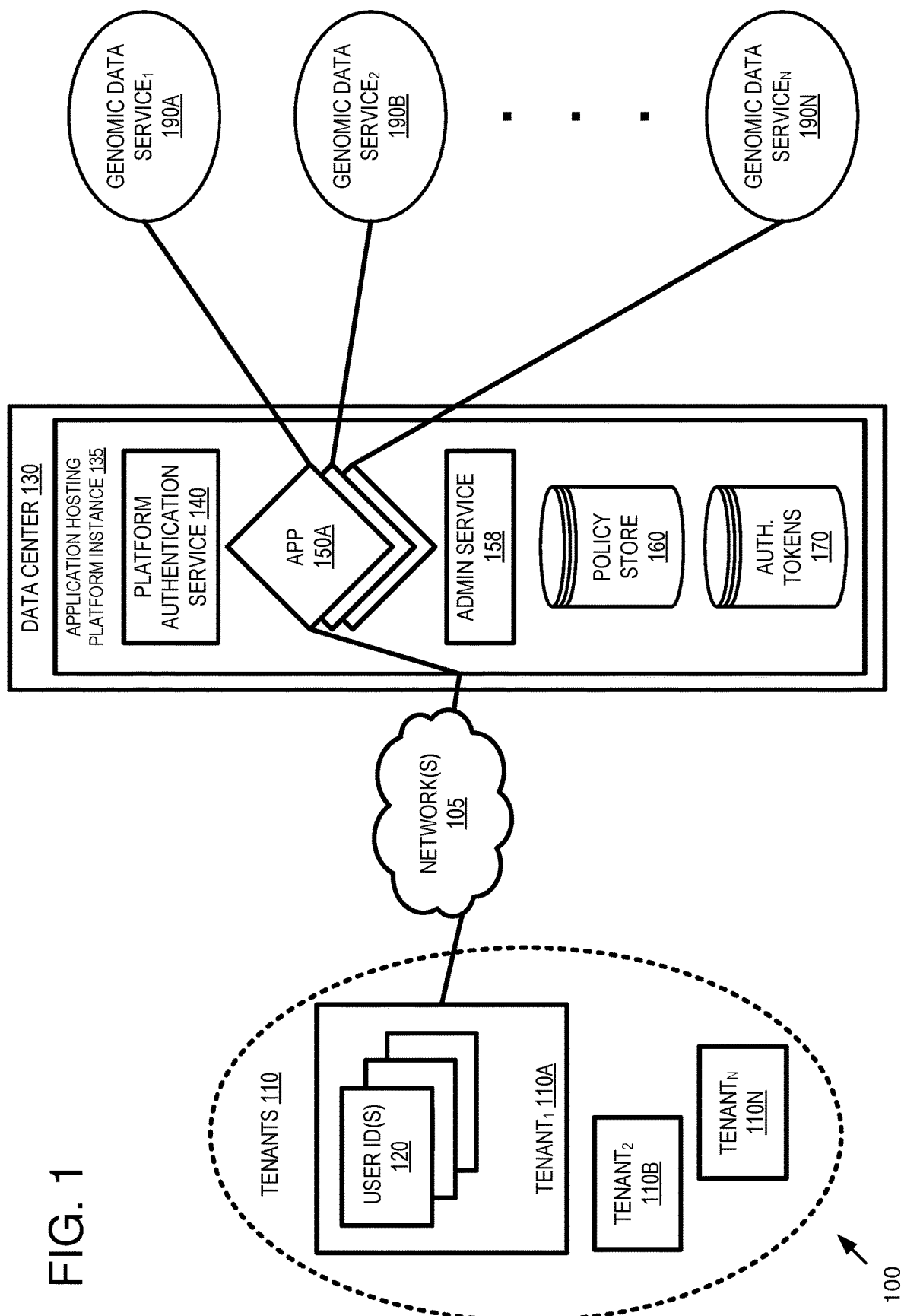
FIG. 1 is a block diagram of an example system implementing policy-based genomic digital data sharing.

FIG. 1 is a block diagram of an example system 100 implementing policy-based genomic digital data sharing. In the example, a plurality of tenants 110A-N with associated user identifiers 120 access an application hosting platform instance 135 running on a data center 130. The platform instance 135 comprises a platform authentication service 140, a plurality of hosted applications 150A-N, an administrative service 158, a policy store 160 (e.g., with policy documents as described herein), and authentication tokens 170. As described herein, some scenarios can involve trust documents (not shown) that can influence policy-based access to genomic digital data.

The applications 150A-N as part of processing can access one or more genomic data services 190A-N, which typically provide genomic digital data.

In practice, the systems shown herein, such as system 100, can vary in complexity, with additional functionality, more complex components, and the like. For example, plural data centers 130 can be implemented, and such data centers can implement plural application hosting platform instances 135. Additional components can be included to implement security, redundancy, load balancing, report design, and the like.

The described computing systems can be networked via wired or wireless network connections, including the Internet. Alternatively, systems can be connected through an intranet connection (e.g., in a corporate environment, government environment, or the like).

The system 100 and any of the other systems described herein can be implemented in conjunction with any of the hardware components described herein, such as the computing systems described below (e.g., processing units, memory, and the like). In any of the examples herein, the genomic digital data, policy documents, authentication tokens, and the like can be stored in one or more computer-readable storage media or computer-readable storage devices. The technologies described herein can be generic to the specifics of operating systems or hardware and can be applied in any variety of environments to take advantage of the described features.

Example 3—Example Method Implementing Policy-Based Genomic Digital Data Sharing

Figure 2:
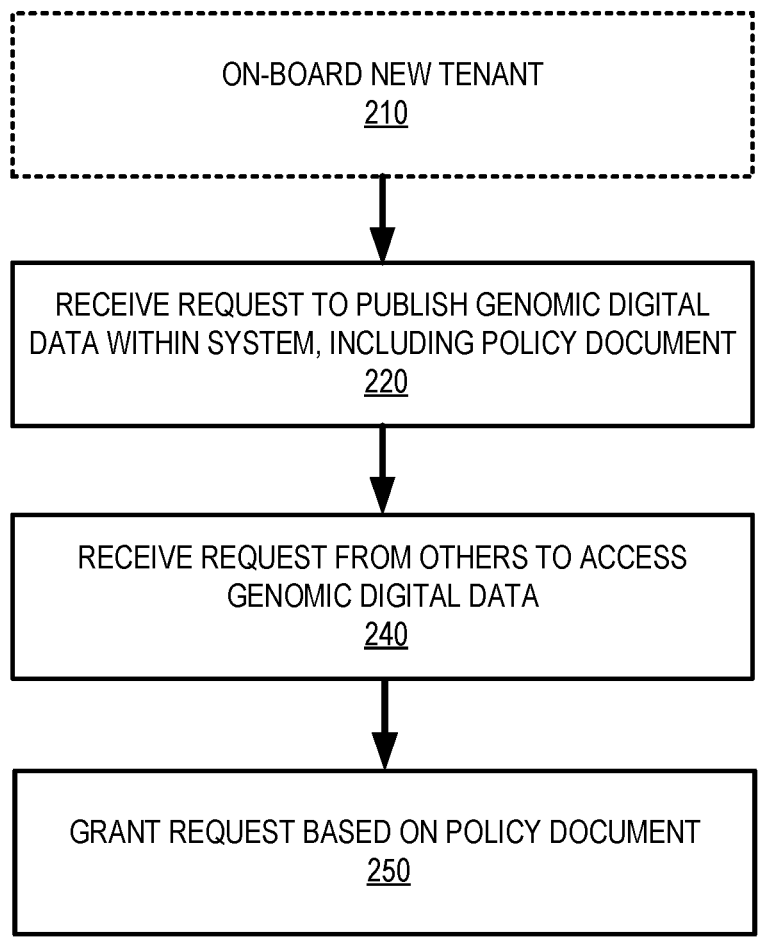
FIG. 2 is a flowchart of an example method of implementing policy-based genomic digital data sharing.

FIG. 2 is a flowchart of an example method 200 of implementing policy-based genomic digital data sharing and can be performed, for example, by the system of FIG. 1 (e.g., the application hosting platform instance 135).

At 210, a new tenant 210 is on-boarded. As a result, the tenant is assigned a tenant identifier and given the ability to share genomic digital data via the tenant identifier. In practice, such on-boarding can be performed any time in advance of receiving requests to publish data for sharing and need not be considered part of the publishing/access scenario.

At 220, the platform receives a request from the tenant to publish genomic digital data within the system, and the request comprises a policy document that controls sharing. In a computing system comprising a plurality of tenants seeking access to genomic digital data resources provided by one or more genomic data services in a software-as-a-service platform that orchestrates access to the genomic digital data resources via policy-based access control, a policy-based access control definition (e.g., the policy document) can be received for a first of the tenants for a given genomic digital data resource. The definition can be received from the first of the tenants or another party (e.g., in an external service provider scenario).

At 240, a request to access the shared genomic digital data from another tenant is received. A request is received for access to the given genomic digital data resource from a second of the tenants seeking access to the given genomic digital data resource.

At 250, the request to access the shared genomic digital data is granted based on (e.g., according to) the policy document as configured by the owning tenant (e.g., the tenant who shared the data). Access is granted based on the policy-based access control definition. As described herein, tokens can be provided in request to the access request. The token can be generated based on the relevant policy and then used to control access to the data (e.g., using role identifiers as described herein). Access to the given genomic digital data resource can be controlled by a role identifier linked to the policy-based access control definition.

In practice, a single party (e.g., operating the platform) may perform all the acts shown; however, it is also possible that one party only performs some actions (e.g., on-boarding) while another party performs others (e.g., granting). Division of tasks may also take place along domain lines (e.g., one party performs functions relating to publication, and another performs functions related to granting access).

The illustrated actions can be interpreted from alternative perspectives while still implementing the technologies. For example, "receiving a request" can be also interpreted as "sending a request" from a tenant's perspective.

The method 200 and any of the other methods described herein can be performed by computer-executable instructions (e.g., causing a computing system to perform the method) stored in one or more computer-readable media (e.g., storage or other tangible media) or stored in one or more computer-readable storage devices. Such methods can be performed in software, firmware, hardware, or combinations thereof. Such methods can be performed at least in part by a computing system (e.g., one or more computing devices).

When implemented in computer-readable media, the technologies can comprise computer-executable instructions capable of causing a computing system to perform respective of the method steps.

Example 4—Example Genomic Digital Data

In any of the examples herein, genomic digital data can be the subject of policy-based sharing. Such data can take the form of sequenced DNA, RNA, or the like (e.g., the output of a sequencer, which, in the case of DNA, typically takes the form of a digital representation of strands consisting of four types of nucleotides: adenine (A), cytosine (C), guanine (G), and thymine (T). The nucleotides can be represented digitally in a variety of ways and encodings, but typically have an equivalent string representation of A's, C's, G's, and T's that is used for convenience of description. Although DNA examples are given, RNA sequencing can be used as well. Similarly, the term "genomic" encompasses information from genomes, exomes, and transcriptomes.

In practice, the sequence information is accompanied by other useful information for research, including substantive data, such as a source of the DNA (e.g., demographics of the subject, pathologies of the subject, and the like). Disease and phenotype information can be included and/or associated with the genomic digital data. Sequencing metadata can be included as well (e.g., the machinery/instrument and technology used to sequence the DNA, the date the sequencing was done, sequencing yield, quality metrics, a pointer to the sequencing run records, and the like). Other metadata such as the name of the originating party, legal restrictions, and the like can also be included.

To facilitate sharing, the data can be provided in a common format that allows for analytics and workflows to be used across tenants. Such formats can be proprietary or open formats to facilitate open exchange of information in sharing scenarios.

Policy-based sharing can be extended to other genomic data, such as executable workflow definitions related to genomic digital data and the like. Thus, a tenant can access both the executable workflow for processing genomic digital data as well as the underlying data itself via the policy-based sharing technologies described herein. A shared executable workflow definition may come from one source (e.g., a tenant), while the underlying data comes from the same or a different source (e.g., a same or different tenant). Such executable workflows can relate to protocols that have been established for the sake of reliability, consistency of results, and the like. Thus, for a particular research project, a given executable workflow may be shared across participants. Custom executable workflows can be developed by tenants and shared as well.

The executable workflow can be executed (e.g., interpreted) by an engine or service that interfaces with sequencing instruments, thereby greatly simplifying, automating, and increasing the reliability and repeatability of the sequencing process. Error recovery and other features can be incorporated into such executable workflows. Workflows can be aimed at a variety of sequencing and related analysis tasks, such as demultiplexing, mapping and aligning, position sorting, duplicate marking, variant calling, and the like. Specialized workflows devoted to tumor-only or tumor-normal modes can be designed for detecting somatic variants in tumor samples. Many other scenarios are possible.

Due to the lengthy compute times and massive volumes of data, such workflows can be employed to deliver quickness, flexibility, and cost efficiency, enabling labs of various sizes and disciplines to take greater advantage of their genomic data. The sharing technologies described herein can greater leverage such data among tenants.

For sake of convenience, shared genomic digital data is sometimes called a "resource" or "protected resource" to denote that the data is a resource to which access is controlled via a policy as described herein.

Genomic digital data can be provided by a genomic data service. Such services can enforce access control and cooperate with the platform as described herein to acknowledge and validate access tokens.

Example 5—Example Software Tenants

In any of the examples herein, a variety of software tenants can be supported. A software tenant is sometimes called a "tenant" for sake of convenience. Such tenants typically take the form of an enterprise tenant, such as a corporation, governmental body, research institution or group, educational institution or group, organization of users, or the like. By taking advantage of the technologies described herein, such tenants can greatly benefit from policy-based sharing.

Any given user of the platform can be assigned to a tenant. In a multi-tenant cloud system, users can share computing resources but have individualized, customizable user experiences and individual stored data. In practice, the tenant tends to represent a separate legal entity that has a separate agreement with the platform provider. Thus, a user identifier is typically associated with a single tenant, and services are provided to the user based on the agreement between the cloud provider and the tenant.

Although the tenants may share computing resources administered by a cloud service provider, a distinguishing factor between tenants is that different tenants can have different subscriptions, different storage restrictions, and access levels to genomic digital data and services of the platform. Various other customizations can be done. Tenants are not necessarily application owners because the application owner can be the cloud provider or a third party. However, some tenants may develop their own applications.

In a cloud-based scenario, a framework is provided transparently to users to leverage redundancy of functionality and process among the tenants. However, boundaries between the tenants can be enforced to prevent access by one tenant to another of the tenant's data. Each tenant's data can be isolated and remain invisible to other tenants. Such an arrangement is typically a basic characteristic of multi-tenant systems. However, while such isolation is typically desirable, for some data there are great benefits to allowing policy-based sharing between tenants as described herein.

Therefore, while the described platform can bear the characteristics of a traditional cloud-based multi-tenant system, it can also allow controlled sharing between and among the tenants, including proxy tenants as described herein.

Example 6—Example Proxy Tenants

In any of the examples herein, a proxy tenant can be implemented. A proxy tenant can be registered as a tenant and have a tenant identifier, but the tenant identifier is not used in the capacity of usual tenant functionality, whether or not the represented entity is an actual tenant of the platform. For example, in a public sharing scenario, a proxy tenant can be set up for the pubic data, whether or not the source (e.g., owner) of data is actually involved (e.g., a website, government agency, foundation, or the like) because the data is public. The proxy tenant has a tenant identifier, and digital genomic digital data can be published under the tenant identifier. In this way, public sharing scenarios can be supported by the platform. In practice, a data-owning proxy tenant may have an actual tenant identifier as well. So, the organization may have multiple tenant identifiers, one in its capacity as a source of public genomic digital data, another in its capacity as a research institution that takes advantage of the usual tenant functionality, and the like.

Similarly, in an external service provider scenario, a proxy tenant can be set up for the external service provider. The external service provider can be assigned a tenant identifier that can be used to access and upload data to the platform for sharing under the tenant identifier. In this way, external service providers can be supported by the system. Again, the external service provider may have an actual tenant identifier as well, which is used when the external service provider is acting in the capacity of a usual tenant.

Finally, the platform administrator or other similar party can operate in the capacity of a tenant or tenant delegate to provide any of the tenant-based functionality described herein. Such an arrangement can be helpful when a tenant does not wish to become involved in the platform or is unavailable or unable to do so.

So, in any of the examples herein, a tenant can be a proxy tenant, and the tenant identifier for such a tenant can be processed according to the technologies described herein to achieve policy-based sharing.

Example 7—Example Roles

In any of the examples herein, roles can be used to control access to shareable genomic digital data. As described herein, a role can be uniquely identified by a role identifier. Such a role identifier can be created when a tenant wishes to publish resources for sharing and be linked to the policy document for a given resource.

Example 8—Example Role Binding

To accomplish the technologies described herein, late binding of a role to a user can be implemented. In a late binding scenario, the user identifier (or tenant identifier of the user identifier) can be bound to a role identifier at execution time (e.g., when access to resources is requested, when a list of available resources is requested, etc.) instead of beforehand. In this way, role assignment can be dynamic in that if the policy changes, a role assignment can also change automatically. Thus, roles can change over time without explicitly specifying a particular user. The user's membership in a tenant or workgroup can cause role assignment to change if the policy references such attributes. As described herein, binding can take place at a time of the request and be based on the user identifier or tenant identifier of the request.

Similarly, policy-based sharing means that any changes to the policy can result in changes to sharing (e.g., role assignment). Policies that further rely on other factors (e.g., agreement status, agreement level, subscription status, subscription level, or the like) can cause a change to role assignment if such factors change. For example, if a tenant acquires a new subscription level, users from the tenant can automatically be granted additional access because a role may be assigned at execution time the next time that a user of the tenant requests access.

Thus, late binding of role and the dynamic nature of role assignment can support a wide variety of flexible, automatic scenarios that avoid individual role assignment to particular users in advance. Resources needed to administer the system are thus greatly reduced while providing such rich functionality.

Additional roles can be provided at the application level (e.g., that are enforced by the application); such roles may have early or late binding. For example, an application role identifier may specify a lab manager, principal, assistant, or the like. The application role identifier can itself be used in a condition statement that controls access to the policy-based role. In such a case, responsive to determining that the access request has attributes indicating a role identifier meeting a condition specified in the policy document, the role is included with appropriate permissions (e.g., as specified for the role) in the signed access token.

Example 9—Example Permissions

In any of the examples herein, permission to share a resource can be specified by specifying a service type, resource type, and permission type (e.g., "GDS.FILES.UPDATE," "GSS.LIBRARYPOOLS.READ," or the like).

Permission types can include, manage, archive, create, delete, destroy, download, hide, lock, read, update, write, admin, run, grant, or the like. Resource types can include subscriptions, files, sequencing runs, library pools, library prep kits, analysis versions, task versions, tasks, runs, workflows, and the like.

Service types can include genomic data services, workflow execution services, and the like.

Example 10—Example Platform

In any of the examples herein, the infrastructure that provides policy-based sharing is sometimes called a "platform." Such a platform can be integrated into a multi-tenant cloud-based platform that provides access to a plurality of applications by the tenants. As described herein, such a platform can become a virtual place where tenants can collaborate via the sharing functionality described herein.

The platform can be implemented as a software-as-a-service (SaaS) platform that orchestrates access to the genomic digital data resources via the policy-based access control technologies described herein.

Various portions of functionality can be referred to as being inside or outside of the platform, but either arrangement may be implemented. For example, some functionality can be delegated to other service providers or brought into the platform as desired. In some cases, functionality can be described as being in an authentication service platform, which can be separate from or integrated into the overall multi-tenant cloud-based platform.

Example 11—Example System with Platform Implementing Policy-Based Sharing

Figure 3:
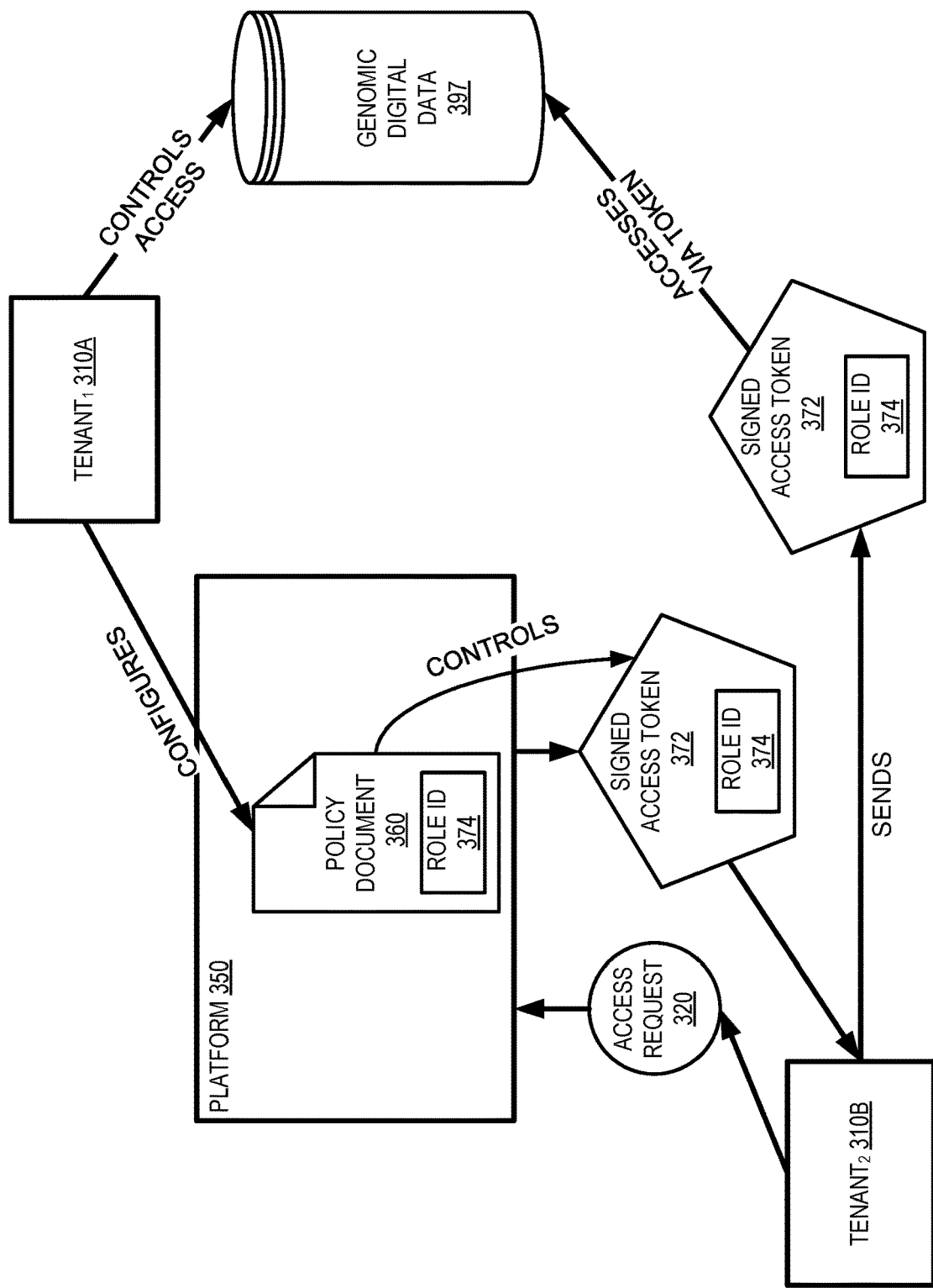
FIG. 3 is a block diagram of an example system comprising a platform implementing policy-based genomic digital data sharing via a signed access token.

FIG. 3 is a block diagram of an example system 300 comprising a platform 350 implementing policy-based genomic digital data sharing via a signed access token 372.

Although an application is not shown, in practice, the actual sharing functionality can be invoked by applications running on behalf of a tenant and requesting access to genomic digital data 397 via the platform 350 and supporting software.

In the example, an owning tenant 310A controls access to the genomic digital data 397. Such control is accomplished by configuring the policy document 360 (e.g., by an administrative user interface). Configuration can include creating a custom role identifier 374 for inclusion in the policy document 360. Such configuration can be included as part of the publication process when the tenant 310A wishes to publish the data 397 for sharing. Although not shown, publication can also include generation of a signed grant token as described herein.

Subsequently, when a tenant 310B wishes to access the data 397, it can do so by sending an request 320 to the platform 350. The policy document 360 controls generation of the signed access token 372 (e.g., which can also include the role identifier 374) as described herein.

The tenant 310B can then send the access token 372 with the role identifier 374 to a genomic digital data service that provides access to the genomic digital data 397 based on the token 372.

Example 12—Example Method of Implementing Policy-Based Sharing

Figure 4:
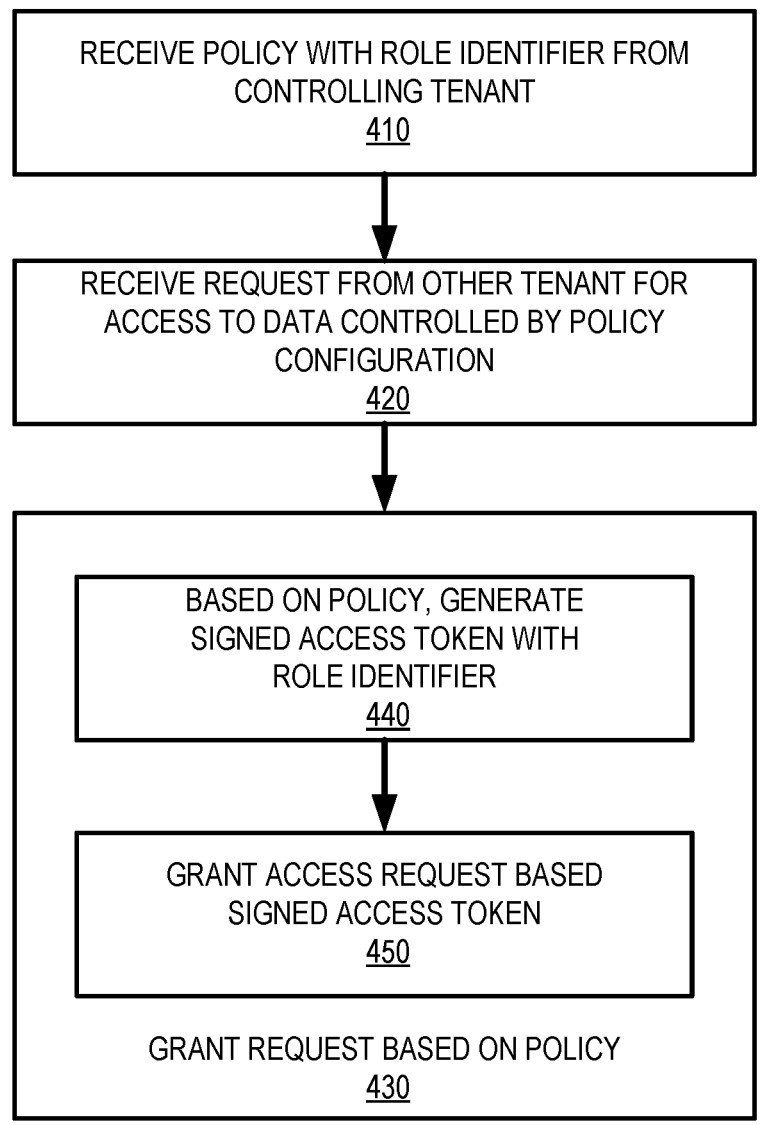
FIG. 4 is a flowchart of an example method of implementing policy-based genomic digital data sharing via a signed access token.

FIG. 4 is a flowchart of an example method 400 of implementing policy-based genomic digital data sharing via a signed access token and can be implemented, for example, by a system such as that shown in FIG. 3 (e.g., by the platform 350).

In any of the examples herein, responsive to receiving a request for access, the role identifier specified in a policy-based access control definition (e.g., a policy document) can be provided for a request for access. The role identifier can then be included in a signed access token.

In the example, at 410, configuration of a policy with a role identifier is received from the controlling (e.g., owner or delegate) tenant.

At 420, a request is received from another tenant for access to data controlled by the policy configuration. As described herein, such request can involve a request for a token.

At 430, the request is granted based on the policy as configured (e.g., a policy document as configured by the controlling tenant). For example, at 440 based on the policy, a signed access token (e.g., with role identifier) can be provided. At 450, the access request can be granted based on the signed access token (e.g., based on the presence of appropriate scope for the role identifier).

Example 13—Example Owning Tenant

In any of the examples herein, the term "owning tenant" can be used to express that the policy-based sharing is essentially tenant-to-tenant-based sharing. An owning tenant can grant access to genomic digital data for which it already has access rights. By publishing data and configuring a policy document, other tenants can then access the data of the owning tenant.

In practice, the owning tenant can delegate sharing administration to another tenant, who can impersonate the tenant for sharing purposes. Thus, the owning tenant is sometimes called the "primary tenant."

Example 14—Example Access Request

In any of the examples herein, an access request can take a variety of forms. For example, the access request can specify the genomic digital data that is desired to be shared (e.g., using an identifier). Alternatively, a general request can be sent, and a list of available resources and associated identifiers can be provided for selection. The access request can then be completed by providing the identifier of the specific resource desired.

In practice, the access request can be provided via communication between an application and a platform providing policy-based sharing services.

A signed access token can be received responsive to the request, and the token is used to actually control access to the protected resource.

In a session-based system, an access request can be sent when the session begins (e.g., the user authenticates), and an access token can be generated based on the user identity. Applications spawned from the session then have access to the resources indicated by roles in the access token.

Example 15—Example Invitation

In any of the examples herein, an invitation process can be used to invite tenants for sharing. For example, a newly on-boarded tenant may receive certain invitations by default. Other tenants may receive an invitation upon signing up for a particular application or service. For example, a subscription model for applications can provide access to an application (e.g., and any associated public data shared as described here) upon subscription to the application. Other tenants may receive an invitation as part of being added to a policy document.

In practice, invitations can be controlled by policy documents or other resources that indicate when sharing is initiated.

The invitation process can include legal compliance, identity verification, key exchange, trust delegation, and the like.

Example 16—Example System Generating Signed Access Token

Figure 5:
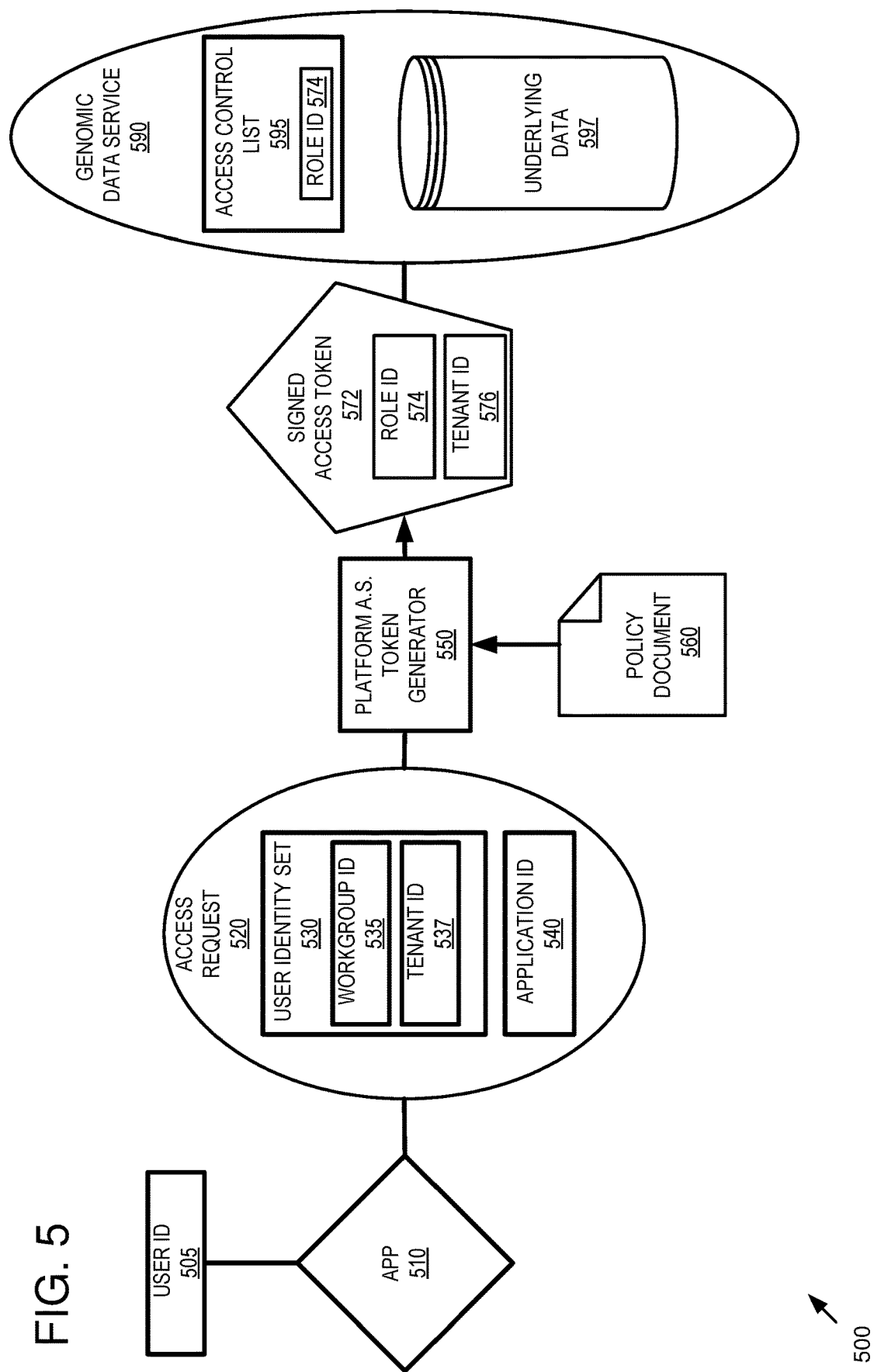
FIG. 5 is a block diagram of an example system generating a signed access token based on an access request and a policy document.

FIG. 5 is a block diagram of an example system 500 generating a signed access token 572 based on an access request 520 and a policy document 560.

In the example, a user identifier 505 of a given tenant is accessing an application 510 that requests access to underlying genomic digital data 597.

The access request 520 can include a plurality of attributes, and in the example comprises a user identity set 530, which includes a workgroup identifier 535, a tenant identifier 537, and an application identifier 540.

The platform authentication service token generator (e.g., of authentication service 140 of FIG. 1 or the platform 350 of FIG. 3), receives the access request 520 as input and generates the signed access token 572 based on the policy document 560. In the example, the user identity set 530 and application identifier 540 support access, so the token 572 includes the role identifier 574 and the tenant identifier 576 of the tenant at issue (e.g., of which the associated user is a user).

The genomic data service 590, when provided the signed access token 572, can validate the token and provide access based on presence of the role identifier 574, which can also be used in an access control list 595 of the genomic data service 590 providing access to the underlying data 597.

Further security can be provided via a grant token as described herein.

Example 17—Example Method of Generating Signed Access Token

Figure 6:
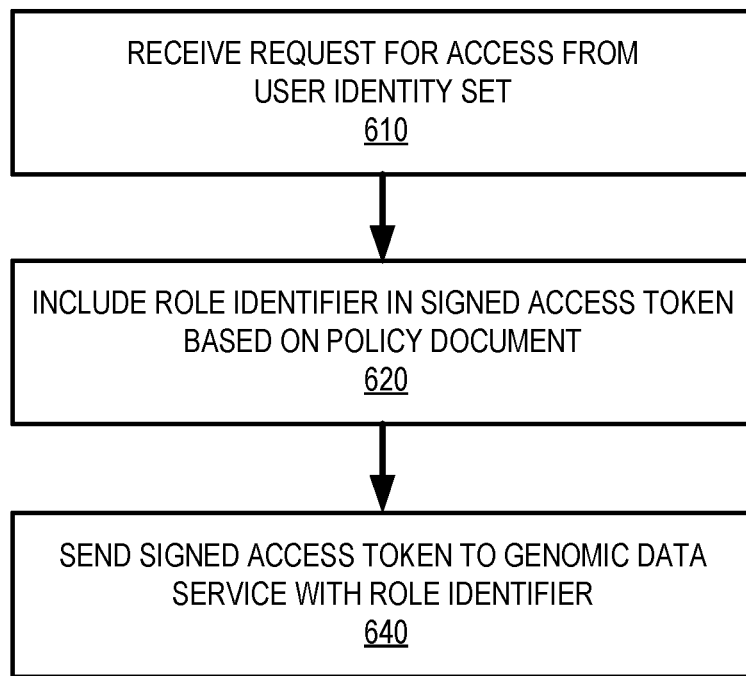
FIG. 6 is a flowchart of an example method of generating a signed access token based on an access request and a policy document.

FIG. 6 is a flowchart of an example method 600 of generating a signed access token and can be implemented, for example, by a system such as that shown in FIG. 5 (e.g., by the token generator 550).

At 610, a request for access is received from a user identity set. In practice, an application being used by a user having the user identity set may actually send the request on behalf of the user identity of the user.

At 620, a role identifier is included in a signed access token based on the policy document associated with the protected resource and one or more attributes of the access request. For example, in a scenario where all tenants using a particular application are granted access, the role identifier can be included responsive to determining that the access request is coming from an instance of the application. If all tenants having the application are granted such access, user identity may not play a part in the decision. However, in a tenant-to-tenant sharing scenario, the tenant identity may be a controlling factor (e.g., the tenant identifier of the requesting tenant must match a condition specified in the policy document). The workgroup identifier of the request may or may not be a controlling factor depending on conditions specified in the policy document.

At 640, a signed access token with the role identifier is sent to a genomic data service.

Access can then be granted to the genomic digital data based on the role identifier.

Example 18—Example Applications

As shown in FIG. 5, an application 510 may send access requests on behalf of the user identifier 505. In any of the examples herein, although a request may be described as coming from a tenant or user identifier, in practice, an application may be operating on behalf of such a tenant or user identifier. The application instance can be associated with an authenticated user identifier and/or tenant identifier, which is used for security purposes (e.g., authenticating requests, determining tenant identifier, determining workgroup identifier, and the like).

Such applications can take a variety of forms and can be used for the acquisition, management, and analysis of genomic digital data as described herein.

Example 19—Example Supported Scenarios

Figure 7:
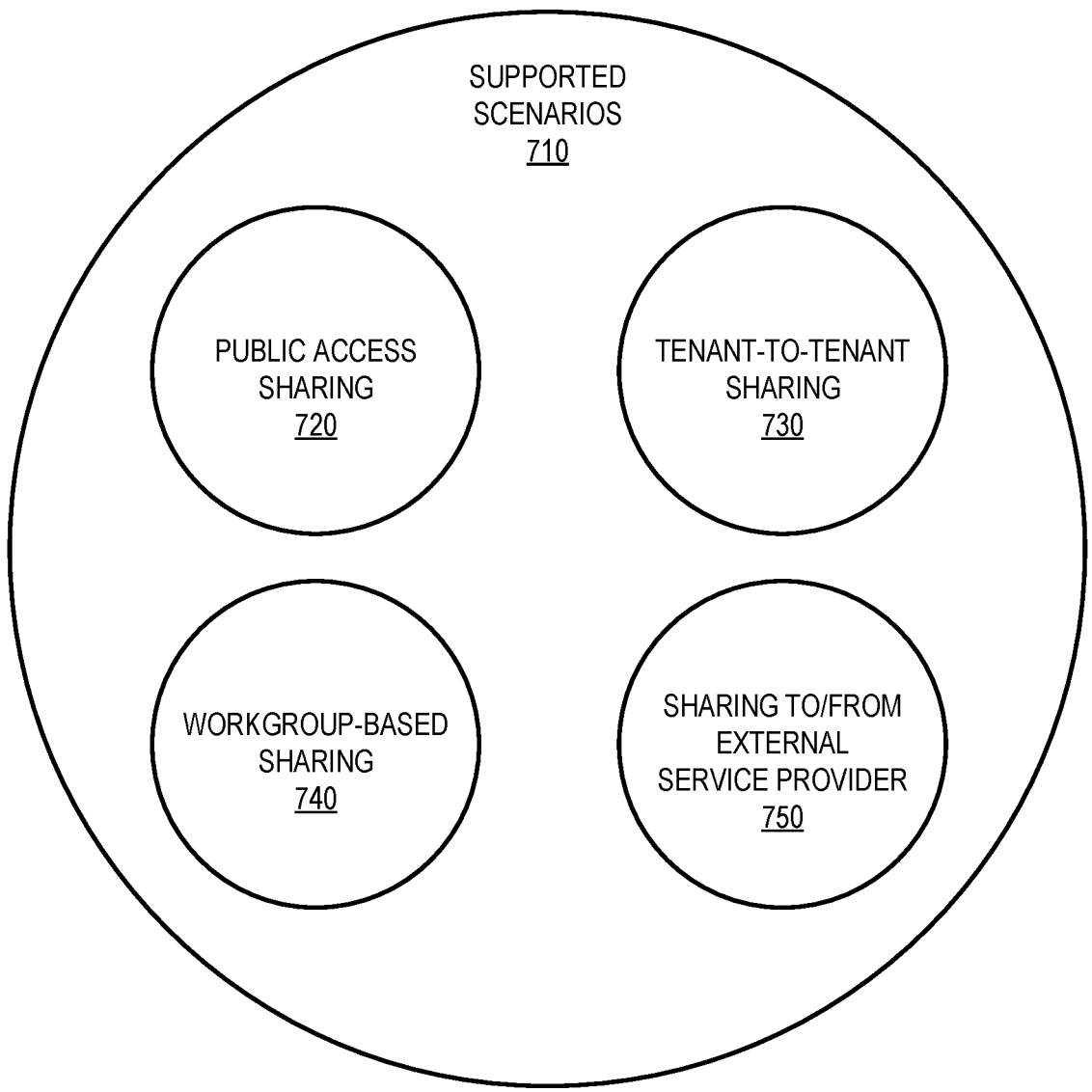
FIG. 7 is a visualization of supported scenarios.

FIG. 7 is a visualization 700 of supported scenarios 710 that can be implemented via the technologies described herein.

Public access sharing 720 can be implemented as described herein by publishing genomic digital data that is public or desired to be public under a tenant identifier that is used to configure a policy document stating that the data is available (e.g., to all users, all users of a given application, or some other criteria).

An example of public access sharing can be implemented with respect to an application. So, for example, any tenant who subscribes to a particular application can be granted access a collection of public data in a format compatible with the application. In such a case, the policy document can specify that requests from the application (e.g., "application: Olympia") for all tenants (e.g., "tid:*") are granted access to the shared public data.

Tenant-to-tenant sharing 730 can be implemented as described herein by publishing genomic digital data under a tenant identifier that configures a policy document specifying conditions controlling sharing (e.g., which other tenants can access the data). Although an invitation process can be involved, the other tenants need not configure the role identifier because the controlling tenant can do so.

Workgroup-based sharing 740 can be implemented as described herein by publishing genomic digital data under a tenant identifier that configures a policy document specifying conditions controlling sharing (e.g., which one or more workgroups can access the data). Although an invitation process can be involved, the members of the workgroup need not configure the role identifier because the controlling tenant can do so. A workgroup can be intra- or inter-tenant (e.g., span across a plurality of tenants).

Sharing to/from an external service provider 750 can also be implemented as described herein by creating a special tenant identifier for the external service provider, even if they are not acting in the capacity as a tenant proper. In this way, external service providers can access genomic digital data on the platform, perform analysis on it and publish results back to the platform for access by the tenant (e.g., who requested that the external service provider perform the analysis).

Other scenarios are possible because the policy documents can include a rich set of conditions that permit sharing. Evaluation of the policy document at execution time can be used so that mass re-configuration of individual user roles by tenant administrators can be avoided.

Example 20—Example Workgroups

In any of the examples herein, any number of users can be assigned to be members of a workgroup identified by a workgroup identifier within the platform. Such users can be of the same tenant or span across tenants. Membership in the workgroup can be controlled by an administrator or programmatic process.

Example 21—Example Token Signatures

In any of the examples herein, an access or grant token can be digitally signed by the controlling tenant for authentication. In practice, a public-private key cryptography approach can be used, where the token is signed with the tenant's private key and authenticated with the tenant's public key.

In practice, the keys of a platform administrator or a delegate can be used in place of the tenant's key to simplify administration. Any keys that are trusted and verifiable by the platform can be used to achieve a trust relationship that is enforced to prevent unauthorized sharing between the tenants.

Example 22—Example Policy Document

In any of the examples herein, a policy document can be used to control sharing. Such a policy document can thus serve as a policy-based access control definition. As described herein, the policy-based access control definition can be evaluated at a time a request for access is received.

FIG. 8 is a block diagram of an example policy document 860 that can be used in any of the examples herein. In practice, the policy document 860 is configured (e.g., created, read, updated, or deleted) by the tenant controlling the resource (e.g., genomic digital data) with which the policy document 860 is associated in the platform. For example, an administrative user interface can be provided for access by an administrator user of the tenant or configuration can be done programmatically if desired.

As described herein, a policy document 860 can filter access requests based on application identifier or name, identity (e.g., tenant identifier, workgroup identifier, or the like), or the like. Although not shown, the policy document 860 can be linked (e.g., mapped) to a role identifier (e.g., controlled by the configuring tenant), and the policy document 860 thus accomplishes control over access by serving as a gatekeeper to the role identifier, which can ultimately be used to authorize access to the protected sharable resource.

A variety of formats can be used to accomplish filtering. In the example, the policy document 860 can include metadata 861 (e.g., a date, version, or the like) and one or more statements 862. The statements can take the form of an effect, a tenant identity parameter 863 and zero or more conditions 864. The effect can specify that the effect takes effect if the identity parameter 863 and the conditions 864, if any, are met. Such an effect can be that sharing is allowed (e.g., "allowed") or that particular types of sharing are allowed (e.g., read-only, read-write, or the like), or permissions as described herein are granted; however, the type of sharing can alternatively be accomplished by creating different role identifiers with differing levels of access.

In practice, the identity 863 is listed separately to emphasize that a tenant identity parameter is typically specified as part of the policy document 860 and effectively serves as a condition. For example, a specific tenant, list of tenants, or wildcard can be listed as the tenant identity parameter. If a request comes in from a tenant identifier satisfying the tenant identity parameter, the parameter is considered satisfied, and the statements will be executed if any conditions 864 are also satisfied.

As described herein, a given condition 864 can include a filter parameter such as application identifier, workgroup identifier, application role identifier, or the like. A request that has attributes that satisfy the condition cause execution of the statement (e.g., which enables access). Thus, access to the underlying role can be filtered based on such attributes.

If the policy document is satisfied, then the linked role identifier is included in the generated access token as described herein.

Additional functionality or configuration can be incorporated into the policy document 860 as desired to extend sharing functionality. For example, a policy document 860 can incorporate or refer to trusted external resources such as smart contracts as described herein.

Example 23—Example Signed Access Token

In any of the examples herein, a shared access token can be generated based on a policy document and the incoming access request to control access to the resource linked to the policy document (e.g., via a role identifier).

Figure 9:
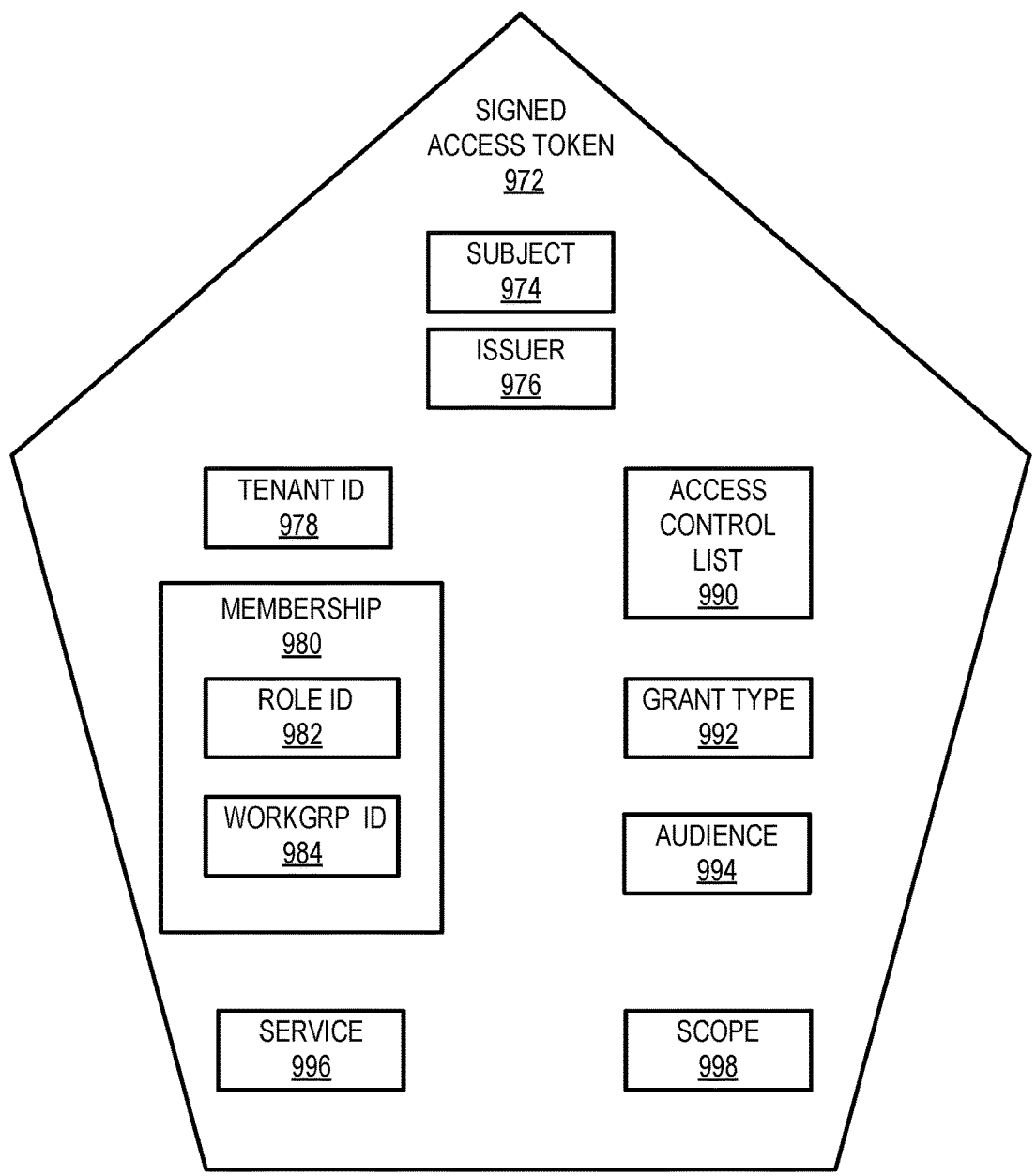
FIG. 9 is a block diagram of an example signed access token.

FIG. 9 is a block diagram of an example signed access token 972 that can be used in any of the examples herein. In practice, an actual token 972 can take different forms with more or fewer fields therein.

The subject 974 can be a system user identifier.

The issuer 976 can indicate which instance of the platform authentication system issued the token. Alternatively, the issuer can be the controlling tenant.

The tenant identifier 978 can indicate the tenant identifier of the user (e.g., the user associated with the application requesting the resource).

Membership can be encoded into the access token 972 based on the user roles and permissions as well as if they user satisfies the policy criteria. During access token generation, a user identifier that fulfils the policy criteria automatically gets the associated role identifier as the membership according to the policy set at the time of granting access. 980 can include the list of memberships that the user has access to. Membership can be indicated by a role identifier 982 and/or workgroup identifier 984. A permission index (or "*" for all) can be included. For example, a user can have membership in both a role and a workgroup.

The access control list 990 can include a tenant identifier and a user identifier along with granted permissions for the associated resources. The access control list in the token 972 can be included for efficiency purposes (e.g., so that a separate access control list need not be checked), or it can serve as a double check on an access control list already in place (e.g., an access control list already shipped to a genomic data service as part of the grant token).

The grant type 992 can indicate the grant type or authentication flow on how the user obtained the token 972.

The audience 994 can determine which cloud provider service the user is attempting to access.

The service 996 can indicate the application or service the user was using to generate the token 972.

The scope 998 can comprise a granted permissions list (e.g., identifiers indicating the granted type of access by specifying a service type, resource type, and permission type (e.g., "GDS.FILES.UPDATE," "GSS.LIBRARYPOOLS. READ," or the like)).

In practice, the signed access token 972 can be implemented as a JSON web token or other format supporting storage of the relevant fields. It can be signed with the signer's private key, allowing authentication via the signer's public key.

Example 24—Example Access Token Generation System

Figure 10:
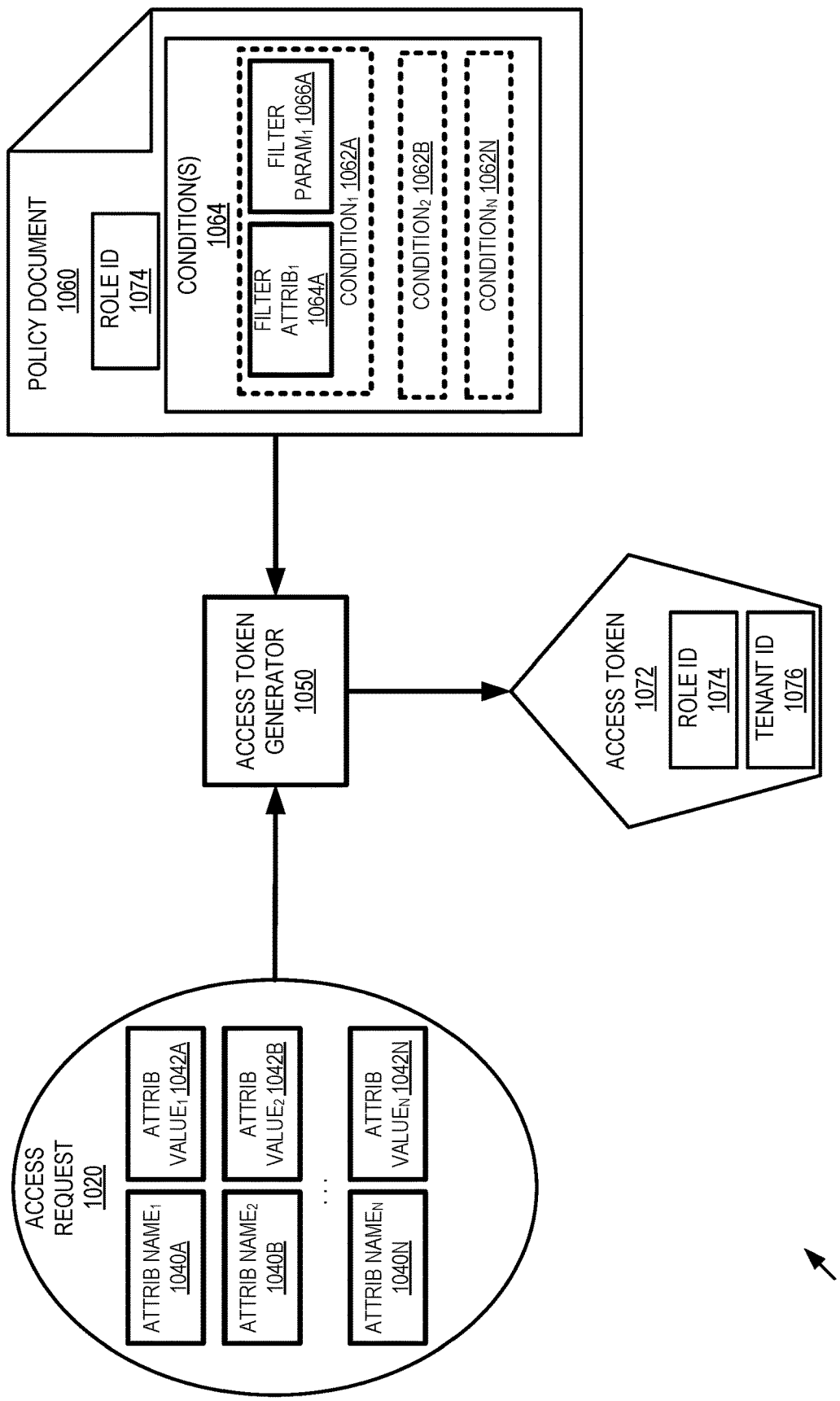
FIG. 10 is a block diagram of an example system generating an access token based on attributes of an access request and conditions of a policy document.

FIG. 10 is a block diagram of an example system 1000 generating an access token 1072 based on attributes of an access request 1020 and conditions of a policy document 1060.

In the example, the access request 1020 can include a set of one or more attribute names 1040A-N-attribute value 1042A-N pairs. For example, attributes can indicate the tenant of the user identifier requesting access, a workgroup, an application associated with the request, or the like.

The policy document 1060 can include a role identifier 1074, which might not be explicitly stored in the document 1060, but instead be linked to it (e.g., in a mapping between role identifiers and policy documents). The policy document 1060 can include a plurality of conditions 1064A-N, including respective filter attribute 1064A-filter parameter 1066A pairs. The filter attribute 1064A can specify an attribute by name or identifier, and the filter parameter 1066A can specify a parameter that indicates which attribute values qualify for assignment of the role identifier 1074. In practice, the parameter 1066A can take the form of a single value, list, wildcard, or the like.

The access token generator 1050 can match the policy parameter to an attribute (e.g., of an incoming request). External conditions can also be included (e.g., conditions that are not part of the access request 1020).

If the access request 1020 qualifies for role assignment as indicated by the conditions 1064A-N, the role identifier 1074 can be included in the access token 1072, along with a tenant identifier (e.g., of the requesting user).

The token 1072 can be signed using a private key (e.g., of the controlling tenant or the cloud service provider). Such signing can be achieved using conventional or other public-private key cryptography methods and could be separate functionality from the token generator 1050. If signed, a public key of the signer can be used to authenticate the token 1072.

Example 25—Example Access Token Generation Method

Figure 11:
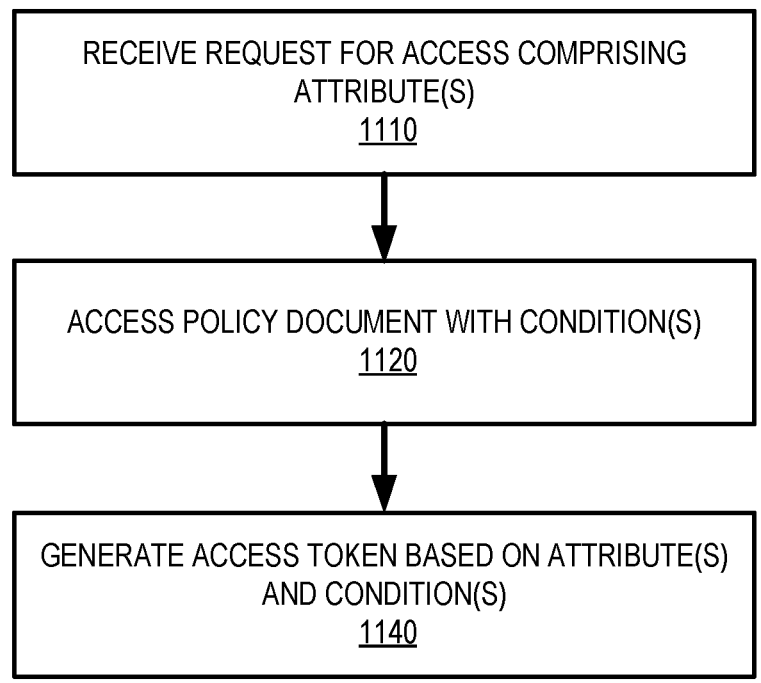
FIG. 11 is a flowchart of an example method of generating an access token based on attributes of an access request and conditions of a policy document.

FIG. 11 is a flowchart of an example method 1100 of generating an access token based on attributes of an access request and conditions of a policy document and can be implemented, for example by the system 1000 of FIG. 10 (e.g., the access token generator 1050 or other access token generating systems described herein).

At 1110, a request for access to shared genomic digital data is received, and the request comprises one or more attributes. Such attributes can take the form of attribute name-attribute value pairs, but the attribute names can be implied (e.g., based on position within the request or the like).

At 1120, a policy document for the shared genomic digital data is accessed, and the policy has one or more conditions.

At 1140, an access token is generated based on the one or more attributes of the request and the one or more conditions of the policy. For example, a role identifier can be included if the attributes indicate that the request meets the conditions of the policy. External attributes can also be included to influence generation of the token (e.g., whether the tenant of the requester has an increased subscription level or the like).

As described herein, the resulting token can be signed.

Example 26—Example Genomic Digital Data Publishing System

Figure 12:
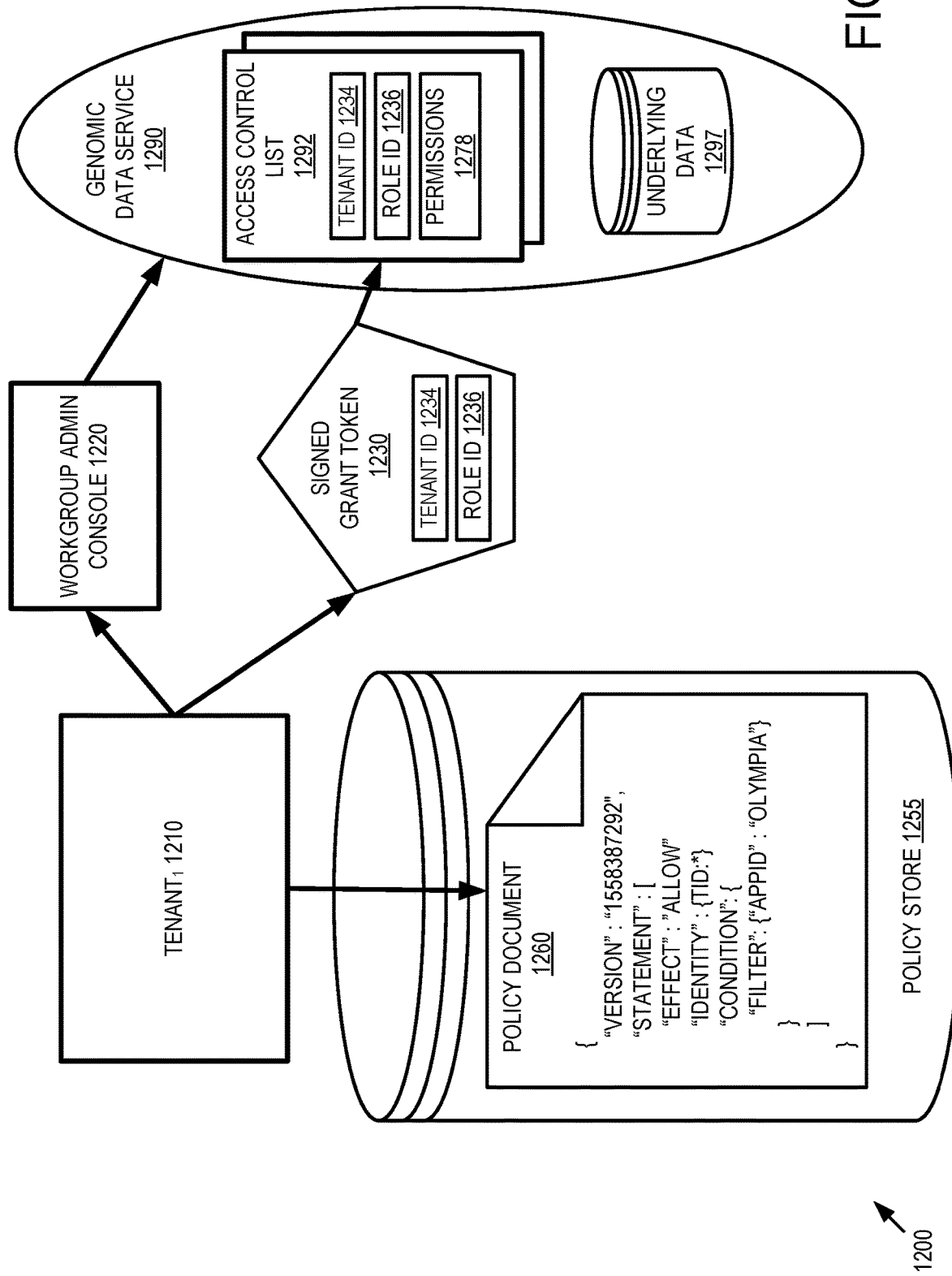
FIG. 12 is a block diagram of a system publishing genomic content for policy-based sharing.

FIG. 12 is a block diagram of a system 1200 publishing underlying data (e.g., genomic digital data) 1297 for policy-based sharing. In practice, the system 1200 can be incorporated into any of the policy-based sharing examples herein and be invoked to configure (e.g., set up) sharing.

In the example, a controlling tenant 1210 accesses a workgroup administrative console 1220 to provide access to shared underlying data 1297 provided by a genomic data service 1290.

An access control list 1292 can be created to enforce restrictions to the data 1297. The access control list 1292 can include an entry indicating the controlling tenant identifier 1234, the role identifier 1236 created for the given policy-based sharing scenario, and the granted permissions 1278 (e.g., indicating resource type, access type, or the like).

The tenant 1210 generates a policy document 1260 that is included in the policy store 1255 and linked with (e.g., mapped with) the tenant identifier of the tenant 1210, the role identifier 1236 and the underlying data 1297.

In the example, the policy document 1260 includes metadata about a version and a statement that allows access to all tenants (e.g., "TID:*") that are accessing the data via the application "Olympia." A signed grant token 1230 is created that includes the one or more access control lists dictated by the publishing scenario. In this way, the access control lists can be shipped to the genomic data service 1290, where they are stored for future reference (e.g., to grant permissions based on requests associated with the role id 1236). In the example, the tenant identifier 1234 of the controlling tenant and the role identifier 1236 created for the policy-based sharing scenario are included.

The illustrated scenario is sometimes called "publishing" the data (e.g., data 1297) because the tenant 1210 has made the data available to those who qualify (e.g., by those requests meeting the conditions in the policy 1260).

Example 27—Example Genomic Digital Data Publishing Method

Figure 13:
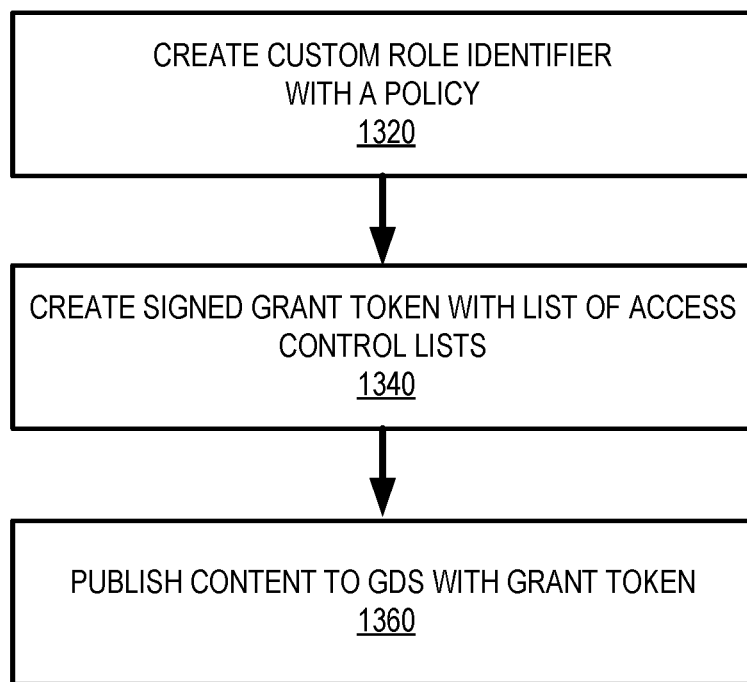
FIG. 13 is a flowchart of an example method of publishing genomic content for policy-based sharing.

FIG. 13 is a flowchart of an example method 1300 of publishing genomic content for policy-based sharing and can be implemented, for example, by the system 1200 of FIG. 12 (e.g., the workgroup admin counsel 1220 or other part of the platforms supporting policy-based sharing described herein). As described herein, the method 1300 can be driven by the tenant granting access (e.g., a workgroup administrator).

At 1320, a custom role identifier is created (e.g., along with a policy document linked to the role identifier). Such a role identifier can be unique within the platform and is allocated in response to the publication request.

At 1340, a signed grant token is created with a list of access control lists. The grant token can be associated with (e.g., linked to) a resource identifier that identifies the genomic content as described herein.

At 1360, the content is published to the genomic data service with the grant token. For example, the data can be uploaded to the genomic data service if not already present. The grant token can be validated to control access to the protected resource.

Example 28—Example Genomic Digital Data Accessing Method

Figure 14:
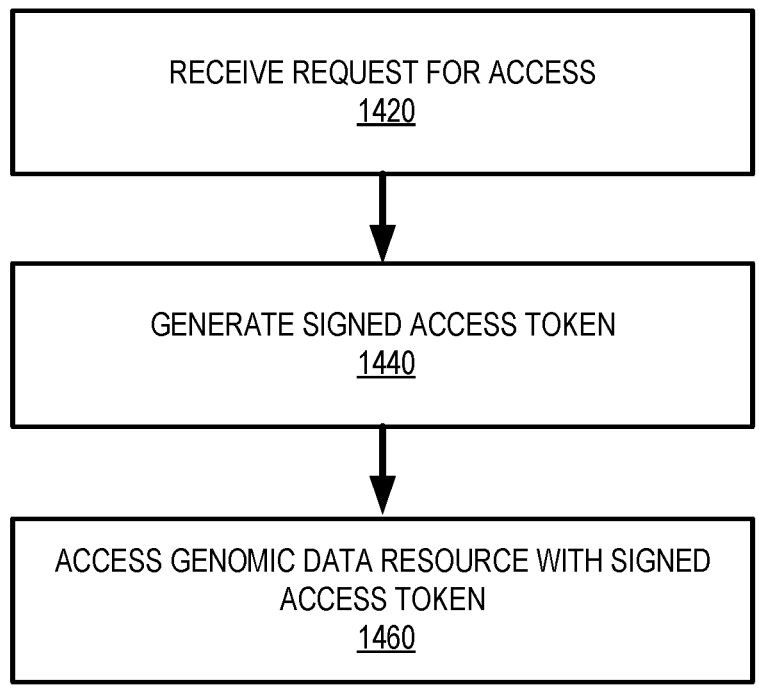
FIG. 14 is a flowchart of an example method of accessing published, shared genomic content.

FIG. 14 is a flowchart of an example method 1400 of accessing published, shared genomic content and can be implemented, for example, by any of the systems supporting policy-based sharing described herein. Such a method is typically driven by the enterprise user identifier accessing the resource.

At 1420, a request for access is received (e.g., by the platform from an accessing user identifier of a given accessing tenant).

At 1440, a signed access token is generated as described herein (e.g., based on the policy).

At 1460, the genomic digital data resource is accessed with the signed access token. For example, requests can be sent to a genomic data service, and the genomic data service responds with the data.

Example 29—Example External Service Provider Registration Method

Figure 15:
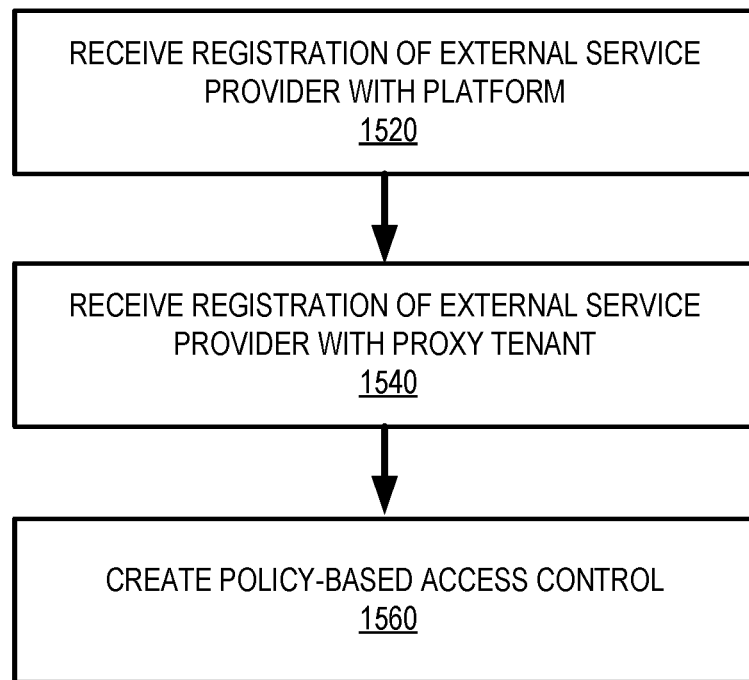
FIG. 15 is a flowchart of an example method of registering an external service provider.

FIG. 15 is a flowchart of an example method 1500 of registering an external service provider and can be implemented, for example, by any of the systems supporting policy-based sharing described herein. Such a method 1500 is typically driven by an administrative user identifier or process. As described herein, a variety of external service provider scenarios can be supported.

At 1520, a registration of the external service provider with the platform is received (e.g., by the platform). Such registration can include scopes and grants of access and can be performed by an administrative user.

At 1540, registration of the external service provider as a proxy tenant is received. A tenant identifier can be used for the proxy tenant, even though the external service provider may not be acting in the capacity of a tenant or participate as a full tenant of the platform.

At 1560, policy-based access control is created (e.g., tenant-to-tenant sharing is enabled via a role created under the proxy tenant of the external service provider). A policy can be associated with the role. In practice, the data is considered to be owned by the external service provider (via the proxy tenant identifier), and the data is shared with accessing tenants via policy-based sharing as described herein.

A more detailed use case is described in FIG. 21 below.

Example 30—Example External Service Provider Integration Method

Figure 16:
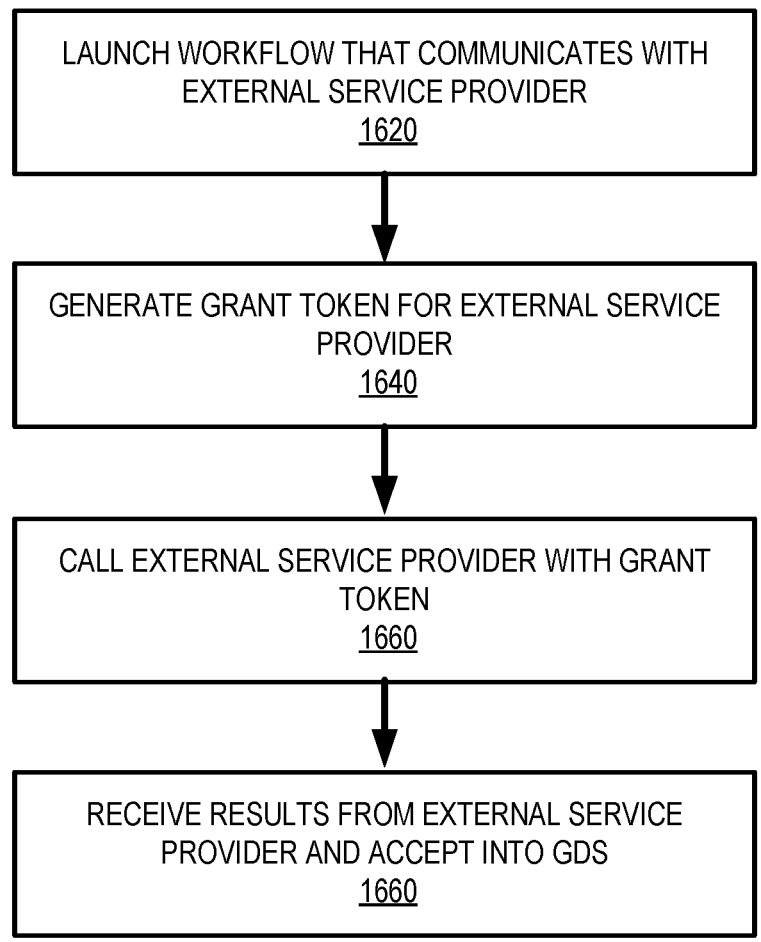
FIG. 16 is a flowchart of an example method of integrating an external service provider into a policy-based sharing platform.

FIG. 16 is a flowchart of an example method 1600 of integrating an external service provider into a policy-based sharing platform and can be implemented, for example, by any of the systems supporting policy-based sharing described herein. Such a method 1600 is typically driven by an accessing user identifier (e.g., from another tenant) or process.

At 1620, a workflow is launched that communicates with the external service provider. Such a workflow can be kicked off to perform tasks associated with the external service provider. For example, a tenant may have sent out a physical biosample and wishes to receive digital genomic data results of analysis of the biosample, a tenant may have generated genomic digital data such as sequencing results and wish to have the results interpreted by the external service provider, or the like.

At 1640, a grant token is generated for the external service provider (e.g., for the particular sharing scenario). In practice, a workflow execution service executing the workflow can request generation of the grant token.

At 1660, the external service provider is called with the grant token, which is validated (e.g., using the administrative public key).

At 1660, results (e.g., of biosample analysis, data analysis, or the like) are received from the external service provider and accepted into the genomic data service (e.g., where they can be accessed by users of the tenant who initiated the workflow involving the external service provider). For example, the external service provider uploads the results to the genomic data service using a signed access token that was provided by or on behalf of the requesting tenant.

A more detailed use case and sample policies are described in FIG. 22 below.

Example 31—Example External Service Provider

In any of the examples herein, an external service provider can be a service provider that provides a genomic data service to tenants of the system. Thus, a tenant for which a policy-based access control definition is received can be a proxy tenant representing an external service provider for which policy-based sharing is implemented. Because the external service provider is operating external to the system (e.g., not as a tenant of the system), a proxy tenant identifier can be set up for use by the external service provider, and the external service provider can be registered with the platform as associated with the proxy tenant identifier. As described herein, the external service provider can then take advantage of the policy-based tenant-tenant sharing technologies described herein.

Such service providers can perform useful services such as analyzing a physical biosample and uploading analysis results (e.g., digital genomic data), analyzing genomic data (e.g., using mathematical processes, machine learning, and the like), and the like.

From a user perspective, an external service provider can appear as a third-party application, the services of which are available to users. In this way, a rich research ecosystem can be provided where third-party applications can be interfaced into the platform so that the platform is not limited to only those applications provided by the platform orchestrator or other tenants.

Example 32—Example Token Validation

Figure 17:
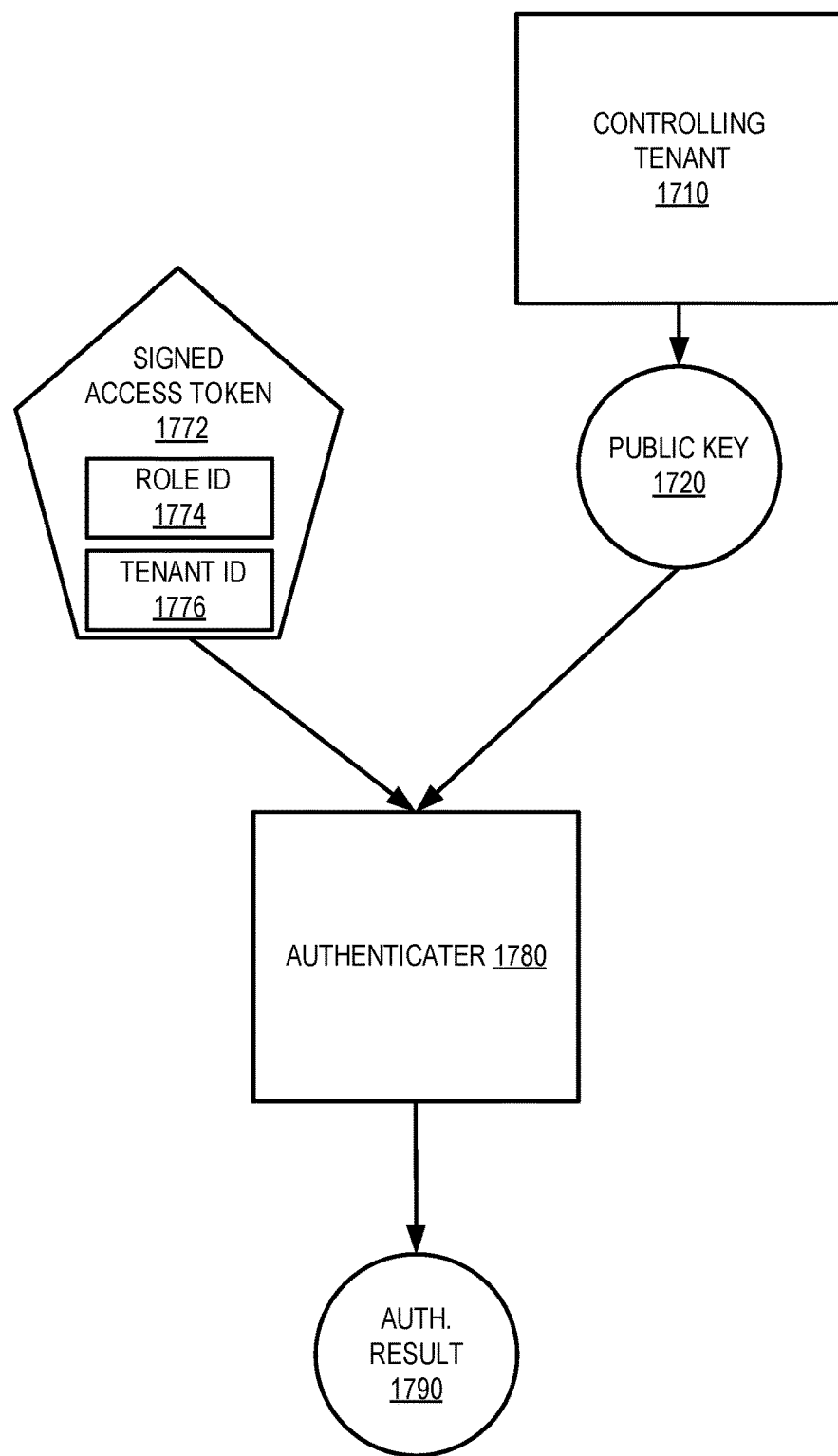
FIG. 17 is a block diagram of an example system validating a signed access token.

FIG. 17 is a block diagram of an example system 1700 validating (e.g., authenticating) a signed access token that can be implemented to achieve token authentication in any of the examples herein. In the example, the signed access token 1772 (with role identifier 1774 and tenant identifier 1776) is signed with the private key of the controlling tenant 1710. In practice, the private key of the controlling tenant can be administered by the tenant or an administrator of the cloud service provider (e.g., the platform orchestrator).

The authenticator 1780 can accept the public key of the controlling tenant 1710 and the signed token 1772, and output an authentication result 1790 (e.g., whether or not the token 1772 was indeed signed by the private key of the controlling tenant 1710). The authenticator 1780 can take the form of conventional public-private key cryptography algorithms (e.g., including hashing and the like) to accomplish validation of the token 1772.

After validation, further processing can be performed to determine whether permissions are available for a given resource (e.g., based on memberships such as role identifier, workgroup identifier, and the like). Responsive to determining that the memberships satisfy specified conditions (e.g., satisfy the access control list), the associated permissions (e.g., in the access control list) are granted to the requestor associated with the token.

Although a signed access token 1772 is shown, the system 1700 can also be used for signed grant tokens described herein.

Example 33—Example Genomic Data Implementations

In any of the examples herein, genomic data can take the form of a genomic file types. Such file types can be associated with different genomic data, differentiating between that acquired during sequencing of a genome (e.g., raw data from a sequencing instrument, the assembled genome, and the like), data for assistance during assembly (e.g., a reference genome), as well as data indicating results of comparative genomic analysis. Comparative genomic analysis can include comparison between or among genomes (e.g., files types that indicate single nucleotide polymorphisms, insertions, deletions, structure variants, and copy number variation within a genome as compared to a reference genome).

An example of such a file type is the VCF (SNP) file type. VCF stands for "Variant Call Format." It is a standardized text file format for representing SNP, INDEL, SV, and CNV variation calls. SNPs (Single Nucleotide Polymorphisms) are the most common type of genetic variation among the genomes of people. Each SNP represents a difference in a single DNA building block (e.g., nucleotide). In practice, this is a widely used VCF.

Another example of a file type is the VCF (INDEL) file type. Indel is a molecular biology term for insertions or deletions in DNA. The number of INDELs in human genomes is second only to the number of SNPs. INDELs can play a key role in genetics.

Another example is the VCF (SV) file type. SVs (or Structural Variants) are large DNA sequences that are inserted, inverted, deleted or duplicated within genomes.

Another example is the VCF (CNV) file type. A CNV (or Copy Number Variation) is when the number of copies of a particular gene varies from one individual to the next. Some cancers are believed to be associated with elevated copy number of particular genes.

Another example is the BAM file type. The Binary Alignment Map (BAM) can be the comprehensive raw data of genomic sequencing; it can include the lossless, compressed binary representation of the sequence alignment map. BAM files tend to be about 90-100 gigabytes in size. They can be generated by aligning the FASQ files to the reference genome. A BAM file (.bam) is the binary version of a SAM file. A SAM file (.sam) is a tab-delimited text file that contains sequence alignment data.

Another example is the FASTQ file type. FASTQ files contain billions of entries and are about 90-100 gigabytes in size, making them too large to open in a normal text editor. FASTQ files can be the ultimate raw data.

Another example is a quality control metric file type (e.g., report). Before running any alignment or assembly, it is possible to check the quality of the underlying data. Quality can be checked from within a sequencing program. A quality control analysis can test a number of different metrics and produce a consolidated report. The report can include a simple categorization (e.g., red, yellow, green) to indicate whether results are bad, intermediate, or good.

Example 34—Example Specialized Permissions

In any of the examples herein, specialized permissions for a genomic context can be implemented. For example, permission granularity can be extended to the file type in policy statements. Thus, a policy can specify that different tenants, workgroups, users, or application roles can have different permissions for different genomic file types or different genomic file type categories (e.g., raw sequencing data, assembled genome, reference genome, comparative genomic analysis, or the like).

A specialized so-called "background" permission can allow utilization of the resource (e.g., file type) by applications or other infrastructure without granting read access (e.g., so it is not able to be read directly). For example, granting background permission to a reference genome, allows the reference genome to be used to assemble raw data, determine single nucleotide polymorphisms, or perform other comparative genomics analysis without granting read access to the reference genome itself.

In addition, specialized permissions can be specified for executable workflows. For example, a "high level run only" permission can allow high level visibility of the workflow (e.g., steps, progress of steps, error messages, and the like), without revealing the details of the workflow (e.g., the underlying interpreted code) or allowing modification of the workflow. Thus, a workflow can be shared among tenants without revealing all minor technical details within it.

Example 35—Example Application Implementations

In any of the examples herein, an application can be devoted to facilitating genomics use cases, such as clinical genomics. For example, a cloud-based in vitro diagnostics solution for oncology can be built into an application that supports sample accessioning, wet lab protocol (e.g., extraction, library preparation, indexing/pooling), sequencing, demultiplexing, sequencing quality control, and then secondary analysis, eventually resulting in a report. Secondary analysis can include comparative genomic analysis, such as detecting single nucleotide variants and the like.

Such an application can coordinate a variety of services and unify management of genomic data to allow efficient and accurate collection and analysis of genomic data. For example, a genomic lab service, a workflow service, an event notification service, a task service, and a genomic data store can work in tandem under orchestration of an application that operates in the sharing environment described herein.

Accordingly, different actors working as tenants or external service providers can collaborate and share information using the described policy-based genomic data sharing technologies described herein.

Example 36—Example Smart Contract Integration

Figure 18:
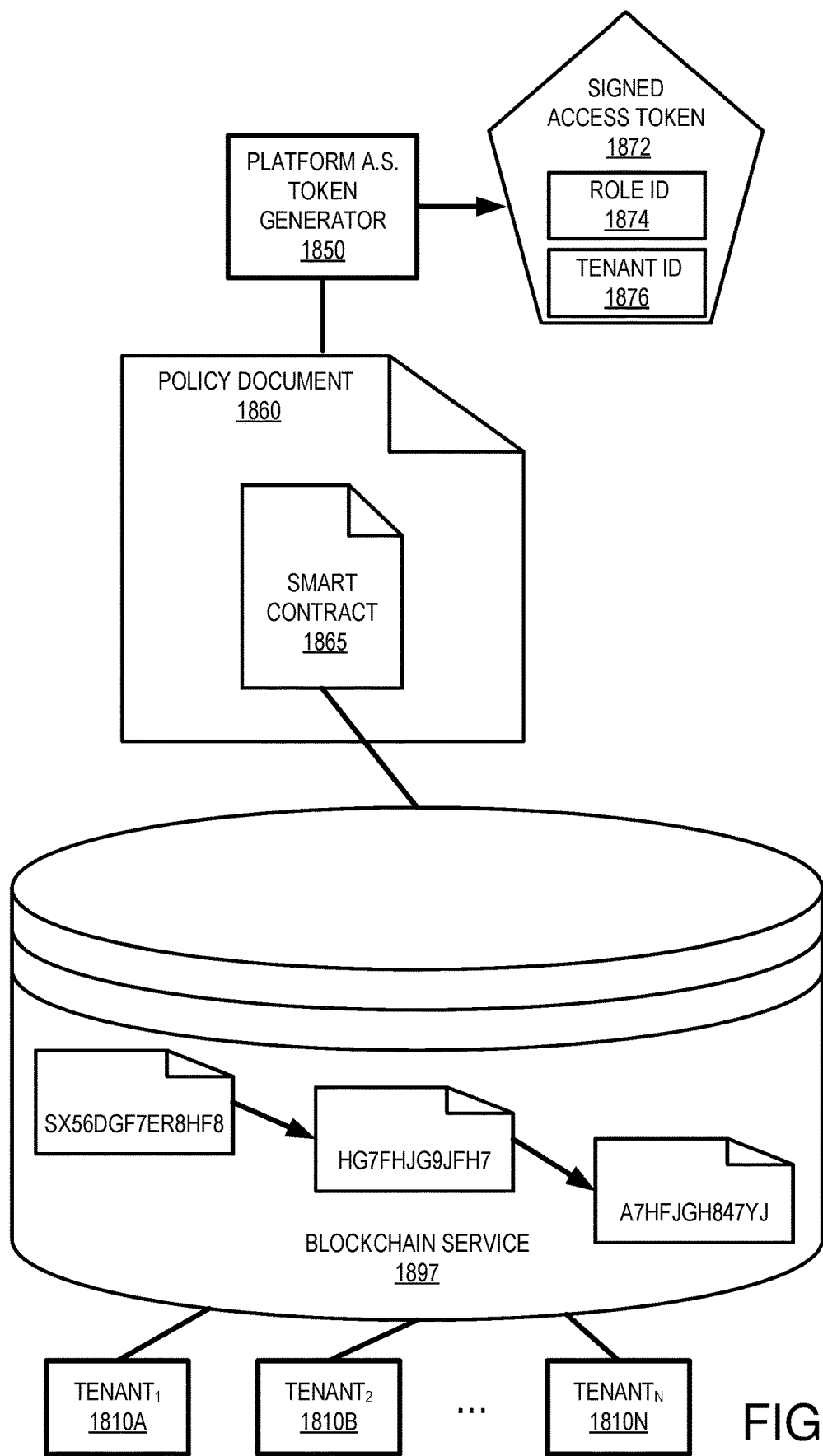
FIG. 18 is a block diagram showing integration of a smart contract into a policy-based sharing platform.

FIG. 18 is a block diagram showing integration of a smart contract 1865 into a policy-based sharing platform that can be implemented to extend policy document functionality in any of the examples herein. A policy can refer to a contract so that whoever satisfies the contract gets access to the data via the policy; conversely, breach or absence of contract satisfaction means that the party does not get access to the data via policy. The party can be specified as a tenant, workgroup, or the like.

In the example, the platform authentication service token generator 1850 consults a policy 1860 to determine how to generate the signed access token 1872 with role identifier 1874 and tenant identifier 1876. As described herein, the generator 1850 can also consult one or more attributes of the incoming request (e.g., a tenant identifier, application identifier, or the like).

As shown, the policy document 1860 can include or reference a smart contract 1865. The smart contract 1865 can itself make reference to a blockchain service 1897 that memorializes agreements for one or more tenants 1810A-N. Such agreements can be between the tenants, between the tenant and the cloud service provider, between the tenant and a third party, or some combination thereof. Such a blockchain service can make use of blockchain techniques such as consensus-based immutable recordation of agreements (e.g., agreement presence, agreement level, service level, or the like) and be built on blockchain infrastructure from any of a variety of providers or technologies (e.g., Ethereum-based functionality or the like).

Trust relationships between the platform and the service, tenant to tenant, and the like can be established via trust documents that can facilitate automated evolution of the policy document 1860 based on agreements indicated by the service 1897.

In this way, whichever tenant satisfies the terms of the contract gets access to the data specified in the associated policy. Automated contract administration is thus provided, facilitating immediate access to the data as specified by the contract upon satisfaction of the contract terms (e.g., payment, subscription, or other terms).

A grant token can be generated based on the completion of a contract, and the access token can be generated when access is requested, in light of the associated policy.

As a further feature, accesses to data can be logged for subsequent auditing functionality. Such logs can indicate the date and time of access, identifier of requesting party, identifier of the granting party, and the policy that permitted access, which itself can be annotated with compliance or legal reasons (e.g., "Agreement of Dec. 15, 2017 between Party X and Party Y") or the like.

Example 37—Example Trust Documents

In any of the examples herein, a policy-based sharing platform can document trust relationships between tenants as trust documents. For example, a trust document can store a consent agreement for one tenant reflecting that trust has been established with another tenant (e.g., by storing an origin tenant, destination tenant, consent agreement date, and consent metadata).

Such a trust document can be enforced as a prerequisite to sharing data with the tenant. For example, in such a scenario, a policy only takes effect if supported by a trust document.

Example 38—Example Smart Contract Method

Figure 19:
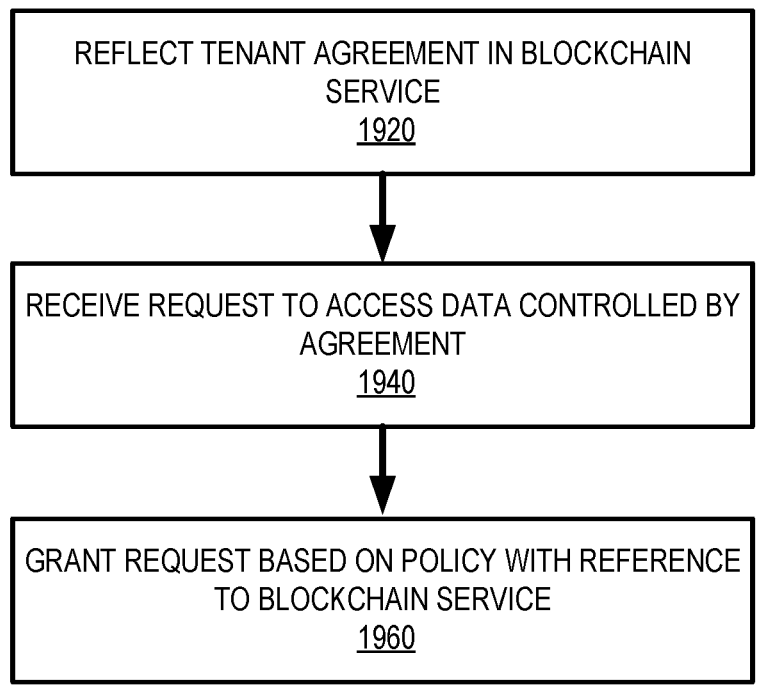
FIG. 19 is a flowchart of an example method of implementing a smart contract in a policy-based sharing platform.

FIG. 19 is flowchart of an example method 1900 of implementing a smart contract in a policy-based sharing platform that can be implemented to extend policy document functionality in any of the examples herein.

At 1920, tenant agreements are reflected in a blockchain service (e.g., provided according to an Ethereum or other blockchain infrastructure).

At 1940, a request to access data controlled by one or more of the agreements is received. For example, a policy with reference to the agreement can be in place for the data.

At 1960, the request to access the data is granted based on the policy with reference to the blockchain service.

At a subsequent point in time, the blockchain service can be updated to reflect an agreement change for the tenant. As a result, the request may no longer be granted, may be newly granted, or the like. In other words, changes to the agreement can result in changes to whether access is granted based on the policy that references the agreement.

Example 39—Example Publishing Use Case

Figure 20:
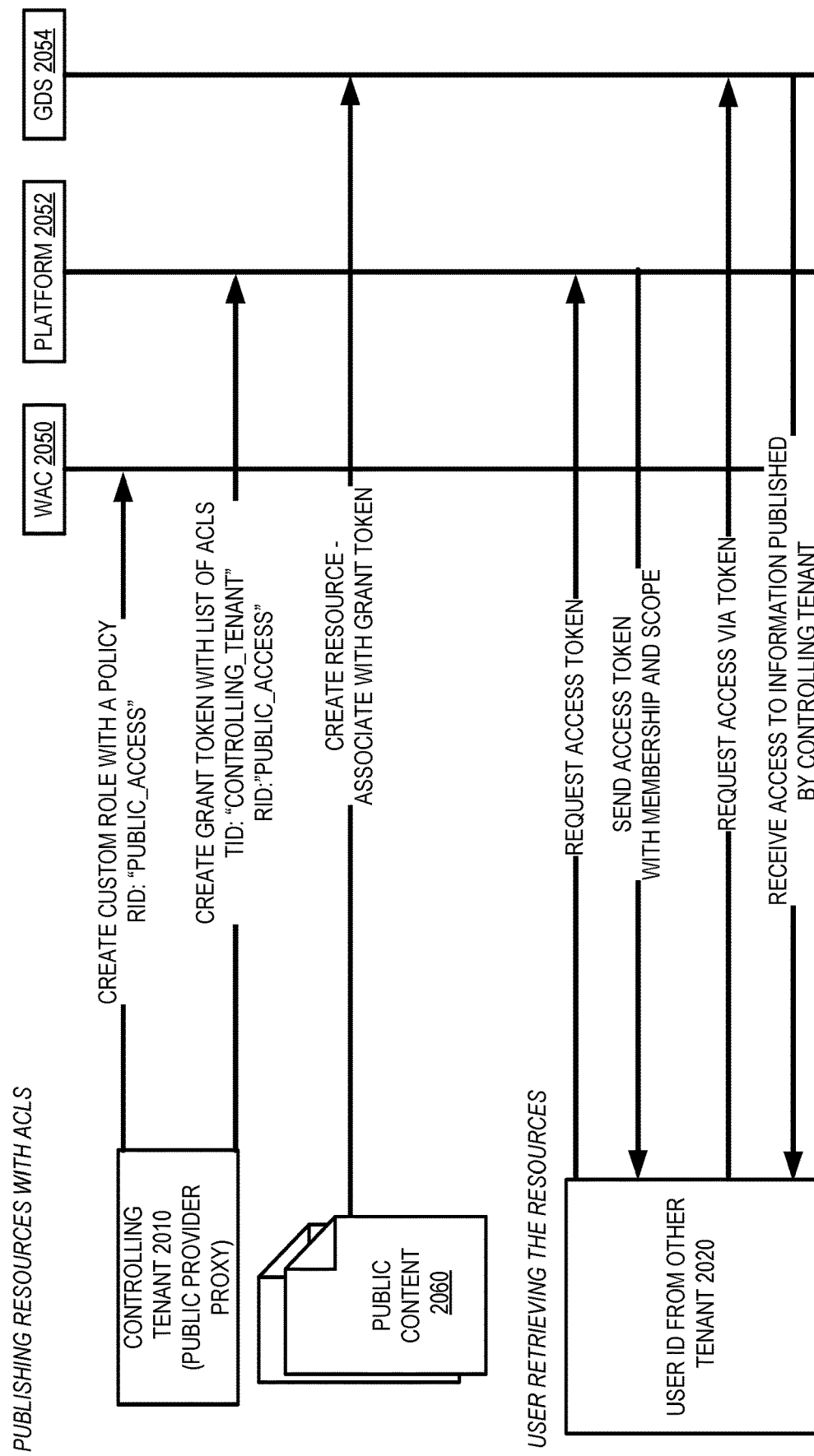
FIG. 20 is a flow diagram of an example publishing use case.

FIG. 20 is a flow diagram of an example publishing use case 2000 that can be implemented in any of the examples herein. Although the example shows "public access," such a use can cover both public and tenant-to-tenant sharing and can parallel the description of the methods of FIGS. 13 and 14.

The initial phase of publishing resources with access control lists can be driven by an administrative user identifier or process. The controlling tenant 2010 can interact with the identity and access management console 2050, the platform 2052, and the genomic data service 2054 to accomplish publication of the public content 2060.

The subsequent phase of retrieving the resources can be driven by a user identifier from another tenant 2020. The access token can include membership (e.g., a role identifier can indicate membership). Receiving access can take the form of receiving a list of resources from which a selection can be made for actual access.

Example 40—Example Grant Token

In any of the examples herein, a grant token can associate a role identifier with a resource (e.g., a resource identifier). The role identifier serves as a policy identity that contains the policy or rules for data access to the associated resource.

For example, a resource identifier can be included in the grant token, associated in a table that maps the grant token to the resource identifier, or otherwise linked to the grant token.

Example 41—Example External Service Provider Use Case

Figure 21:
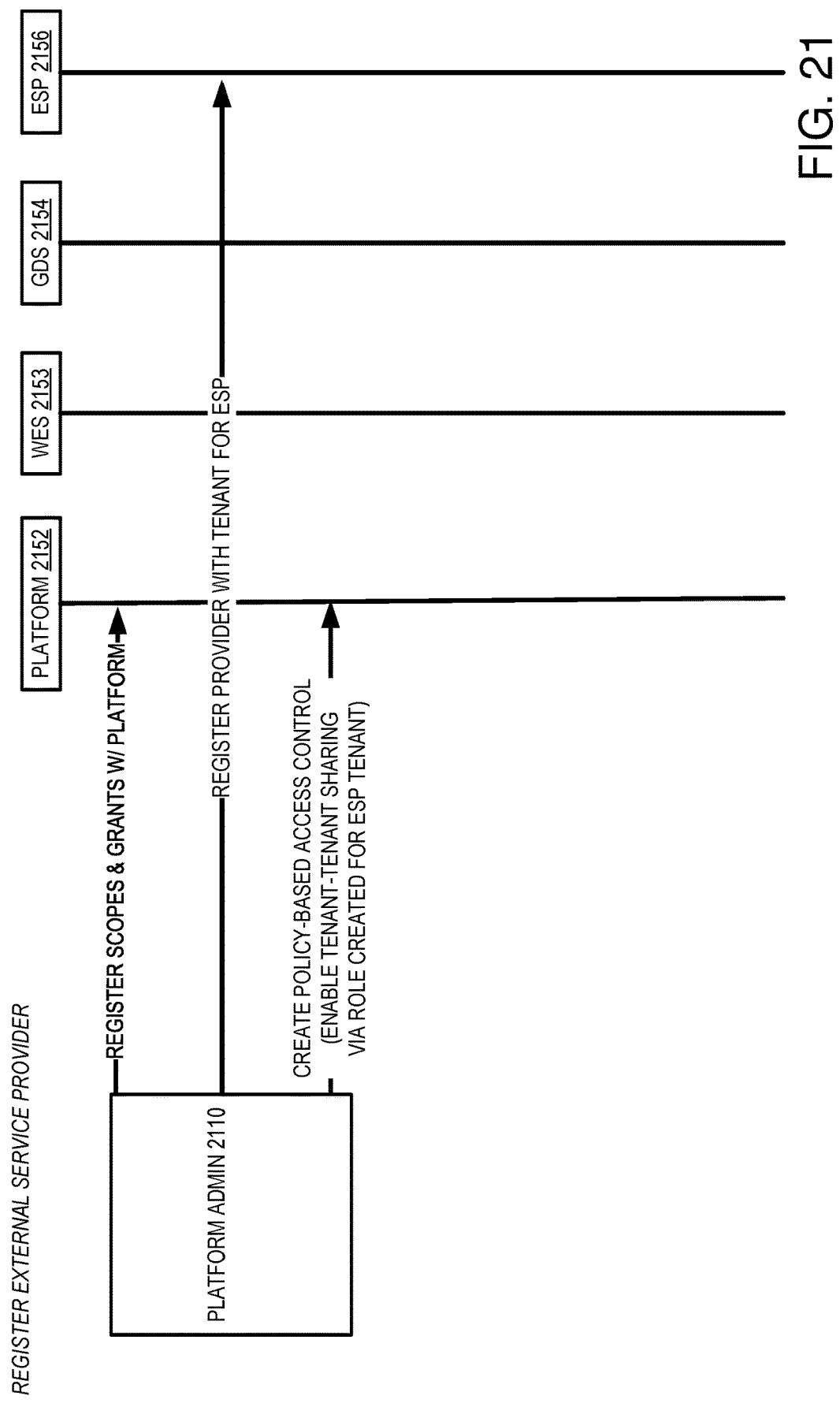
FIG. 21 is a flow diagram of an example external service provider use case involving registration.
Figure 22:
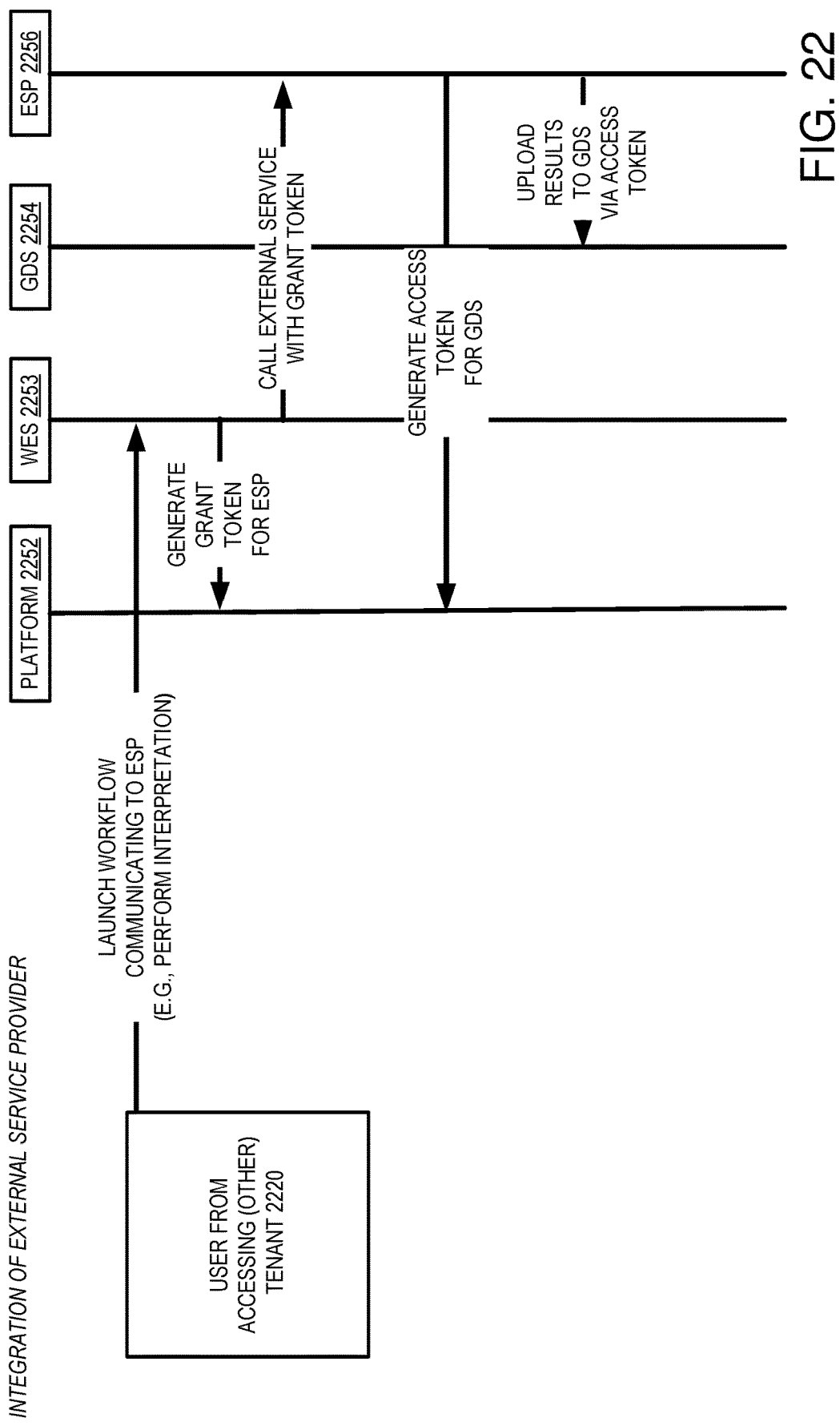
FIG. 22 is a flow diagram of an example external service provider use case involving integration.

FIGS. 21 and 22 are flow diagrams of an example external service provider use case method 2100, 2200 that can be implemented in any of the examples herein. Such a use case can parallel the description of the methods of FIGS. 15 and 16. First, the external service provider is registered (e.g., as a proxy tenant), and then the external service provider is integrated into the system (e.g., policy-based sharing is used to allow an external service provider access to the system, whether read access, write access, or both).

In an external service provider scenario, a single policy can accomplish sharing as described herein. Such a policy can be defined during registration of the external service provider into the platform. Such a policy can comprise information such as with which tenants the external service provider can share data. For example, in a scenario where the external service provider uploads data, the policy can both allow the external service provider to upload the data and allow the accessing tenant to access the data uploaded by the external service provider.

Data generated by the external service provider can go to a dedicated tenant (e.g., "tenant_ESP"), and the platform administrator can define a policy for the dedicated tenant to share data with a tenant that wishes to use external service provider sharing. When the accessing tenant generates the access token, the token is encoded with memberships based on their access rights and the role identifier specified in the policy is dynamically populated in as one of the memberships if the tenant fulfils the policy criteria.

The sharing scenarios can be used to support workflows involving the external service provider. Typical workflows that can be initiated are for the external service provider to upload genomic results from analysis (e.g., of a physical biosample), the external service provider to download genomic data and upload results of analyzing the genomic data (e.g., download genomic data, process the genomic data externally, and upload the analysis results), and the like. For example, a tenant may wish to take advantage of an external service provider that generates a variant report based on output from a sequencing process (e.g., sample files that contain base call and quality information for reads passing filtering, such as FASTQ files). A tenant can run a workflow with the external service provider to upload the sample files to the external service provider. After upload, the external service provider can run their process and generate a variant file to which the tenant then has access.

The platform need not be aware of the inner workings of the external service provider. An input file can be sent, and the external service provider generates an output file, which is shared with the originating policy (e.g., rid:< >) when the file was initially uploaded. In the example, the external service provider can both read and write to the resource (e.g., file storage area).

The initial phase of registering the external service provider with the platform is shown in FIG. 21 and can be driven by a workgroup administrator identifier or process. The administrator user identifier 2110 can interact with the platform 2152 and the external service provider 2156. The workflow execution service 2153 and the genomic data service 2154 can enter in at a later time (e.g., integration, access, or both). Although the administrator user identifier 2110 may be for that of an administrator of the platform, a tenant administrator identifier may be awarded such authority (e.g., to register and integrate external service providers) if desired.

Subsequently, after registration, integration of the external service provider 2156 can be provided as part of the workflow that involves the services of the external service provider 2156. In practice, the data can be owned by a proxy tenant for the external service provider 2156 and shared with other tenants.

In the example, a platform administrator user identifier 2110 registers the external service provider 2156 (e.g., scopes and grants for the external service provider 2156) with the platform 2152.

The administrator user identifier 2110 then registers the external service provider 2156 with a dedicated tenant (e.g., a proxy tenant such as "Tenant_ESP" for the external service provider 2156). In a data writing scenario, external-service-provider-processed data can be streamed to the dedicated tenant, even though the external service provider may not be a full tenant of the system.

The platform administrator user identifier 2110 can then create policy-based access control that enables tenant-tenant data sharing. For example, the proxy tenant can share data with one or more specified tenants.

An example policy that allows the external service provider ("Tenant_ESP") to share its data with Tenant1 is as follows:

```
rid: <tenantESP_tenant1_GUID> (Data Owned by:
Tenant_ESP but data shared with tenant1 with limited
permission Ex : GDS .FILES . READ)
  {
    "Version": "1558387292",
    "Statement" : [
      "Effect" : "allow",
      "scope" : "GDS.FILES.READ"
      "Identity" : { tid: tenant1 }
    ]
  }
```

The policy is associated with the role identifier "tenantESP_tenant1_GUID."

An example policy that allows the external service provider (tenant_ESP) to share its data with the Tenant1_Clinical_Workgroup is as follows:

```
rid: <tenantESP_tenant1_GUID> (Data Owned by : Tenant_ESP
but data shared with tenant1 with limited permission
Ex:GDS.FILES.READ)
  {
    "Version": "1558387292",
    "Statement" : [
      "Effect" "allow",
      "scope" : "GDS.FILES.READ"
      "Identity": { wid: tenant1_clinical_workgroup1 }
    ]
  }
```

The policy is associated with the role identifier "tenantESP_tenant1_GUID."

After completion of registration, integration can be implemented as shown in FIG. 22, which involves the same parties and a user identifier 2220 from an accessing tenant (e.g., Tenant1) that wishes to take advantage of the services offered by the external service provider 2256. In the example method 2200, the user identifier 2220 from the accessing tenant launches a workflow execution task (e.g., that communicates to the external service provider 2256) with the workflow execution service 2253. For example, the task might be entitled "Perform interpretation." In the example, the external service provider 2256 provides results to the accessing tenant, where providing the results comprises uploading the results to the genomic data service 2254, where the accessing tenant can access them.

The workflow execution service 2253 sends a request to generate a grant token for the external service provider 2256 using the proxy tenant identifier (e.g., "Tenant_ESP"). The token includes the access control lists per the policy. The platform 2252 responds with a grant token, which can take the following general form:
  issuer=platform
  audience=esp
  access control list=[rid:< >]
  tenant id=tenant1
  membership={ }

The workflow can then call the external service provider 2256 with the grant token, which can be validated by the external service provider 2256 (the token's intended audience) using a public key of the platform orchestrator or other entity authorized to perform registration.

The external service provider 2256 can then send a request to the platform 2252 to generate an access token for the genomic data service 2254, copying the access control lists from the grant token's access control list claim. The platform 2252 responds with an access token, which can take the following general form:
  issuer=platform
  audience=gds
  access control list=[rid:< >]
  membership={"rid":< >}
  tenant id=tenant_ESP The external service provider 2256 can then upload the results to the genomic data service 2254 using the access token, which can be validated by the genomic data service 2254 (the token's intended audience).

Subsequently, the uploaded data can be accessed by the user id 2220 of the accessing tenant (tenant1) or any other user of the accessing tenant if the user id has the appropriate membership (e.g., rid:<tenantESP_tenant1_GUID>) enabled via policy by the other tenant's administrator user.

An example policy that allows all users in the accessing tenant (tenant1) to see the processed data from the external service provider is as follows:

```
rid: <tenant1_ESP_data_read_access_GUID>
{
   "Version": "1558387292",
   "Statement" : [
     "Effect" : "allow",
     "scope" : "GDS.FILES.READ"
     "Identity": { uid:* }
   ]
}
```

The policy is associated with the role identifier tenant1_ESP_data_read_access_GUID.

Access to the data uploaded by the external service provider is thus achieved by using the tenant-tenant policy-based sharing technologies described herein, where the external service provider is assigned a proxy tenant identifier.

The creator of a policy that has permission rights to resources can thus enable access to any internal or external tenants for a list of identities and the resources.

Example 42—Example Version Field of Policy

In any of the examples herein, the version field of a policy can be used to facilitate audit tracking and rollback policies to a previous version.

Example 43—Example Policies

In any of the examples herein, policies can be used to control sharing. Different policies can be used to achieve different sharing objectives. In the following example, a platform orchestrator "Illumina" maintains a platform that supports a variety of policy-based sharing scenarios.

Policies can be associated with role identifiers that ultimately control access to the shared resources. A policy can contain one or more identities (e.g., user identifier, application identifier, workgroup identifier, group identifier), scopes (e.g., permissions), and a role identifier (e.g., one policy can nest another policy). The policy (rid) can be associated with resources or identities to allow access to the resources.

For example, the following policy can achieve application-enabled content that allows any user that is using a particular application ("Olympia") to access content:

```
rid: <illumina app_enabled_data> (Owned by : Illumina)
{
   "Version": "1558387292",
   "Statement" : [
     "Effect" : "allow",
     "scope" : "GDS.FILES.READ, GDS.FOLDERS.READ, GDS.FOLDERS.WRITE"
     "Identity": {tid:
       "Condition" : {
```

-continued
```
         "filter" : { "appid": "olympia"},
         "filetypes" : [ "sam", "vcf", "bam" ]
       }
   ]
}
```

The policy achieves application-enabled content by including a filter that specifies an application identifier of the application in question. Another filter limits access to certain filetypes specified in a filetype filter (e.g., sam, vcf, bam). As shown, the policy is associated with the role identifier "illumina_app_enabled_data".

In another example, a policy allows public content to be shared with anonymous users who are using a specified application:

```
rid: <illumina_public_data> (Owned by : Illumina)
{
   "Version": "1558387292",
   "Statement" : [
     "Effect" : "allow",
     "scope" : "GDS.FILES.READ"
     "Identity": { tid: * }
       "Condition" : {
         "filter" : { "appid": "olympia" }
       }
   ]
}
```

The policy achieves read-only sharing with any user by specifying a read-only scope and including a wildcard for the tenant identifier. In the example, access is limited to those users using the application ("olympia") specified in the application identifier filter of the policy. However, removing the application filter in the policy would allow read-only access by any user. As shown, the policy is associated with the role identifier "illumina_public_data".

In another example, private content is shared with labs (workgroup) lab001 and lab002:

```
rid: <illumina_private_shared_data> (Owned by : Illumina)
{
   "Version": "1558387292",
   "Statement" : [
     "Effect" : "allow",
     "scope" : "GDS.FILES.READ"
     "Identity": { wid: lab001, wid: lab002 }
   ]
}
```

The policy achieves read-only sharing with any user in the two workgroups by specifying a read-only scope and including an explicit list of one or more workgroups. As shown, the policy is associated with the role identifier "illumina_private_shared_data".

In another example, a tenant user 1 shares data with tenant 2 users having the user identifier "2":

```
rid: <tenant1_private_shared_data> (Owned by :
Tenant1's user- uid:1 )
{
   "Version": "1558387292",
   "Statement" : [
     "Effect" : "allow",
```

```
    "scope" : "GDS.FILES.READ"
    "Identity": { uid: 2 }
  ]
}
```

In the example, the policy achieves read-only sharing with a particular user identifier by specifying a read-only scope and by specifying the user identifier in the identity field. As shown, the policy is associated with the role identifier "tenant1_private_shared_data".

In another example, a workgroup in tenant1 shares data with a user in the tenant2 with restricted permissions (i.e., read files and write files only):

```
rid: <tenant1_workgroup1_private_shared_data> (Owned
by : Tenant1's Workgroup owner)
{
  "Version": "1558387292",
  "Statement" : [
    "Effect" : "allow",
    "scope" : "GDS.FILES.READ, GDS.FILES.WRITE"
    "Identity": { uid: 2 }
  ]
}
```

In the example, the policy is associated with the role identifier "tenant1_workgroup1_private_shared_data".

In yet another example, a workgroup in tenant 1 shares data with another workgroup in tenant2:

```
rid: <tenant1_workgroup1_private_shared_data> (Owned
by : Tenant1's Workgroup owner)
{
  "Version": "1558387292",
  "Statement" : [
    "Effect" : "allow",
    "scope" : "GDS.FILES.READ, GDS.FILES.WRITE"
    "Identity": { uid: 2, wid: 1ab002 }
  ]
}
```

In the example, the policy is associated with the role identifier "tenant1_workgroup1_private_shared_data", which is reused from the previous example. Thus, more than one policy can be associated with a role identifier, allowing stacked policies that can be used to expand access in practice (e.g., a policy can be re-used across role identifiers to grant similar users access to different resources).

As shown, a variety of policies can support a variety of sharing scenarios.

Example 44—Example Security Context

In any of the examples herein, a role identifier (e.g., role ID, rid, or the like) can alternatively be implemented as a security context identifier (e.g., context ID, cid, or the like).

Example 45—Example Collaborating Parties

In any of the examples herein, parties can collaborate on the platform by sharing genomic digital data. As described herein, such parties can be workgroups, tenants, or both. Collaborating workgroups can be intra-tenant workgroups (e.g., one tenant) or inter-tenant workgroups (e.g., one or more workgroups of a tenant collaborate with one or more workgroups of another, different tenant). Parties can include patients, research laboratories, clinical laboratories (e.g., Quest Diagnostics, LabCorp or the like), contract laboratories, medical clinics, hospitals, universities, specialists, counselors (e.g., genetic counselors or the like), companies, genomic services companies (e.g., 23AndMe, Ancestry, or the like), agencies, (e.g., U.S. Centers for Disease Control and Prevention, U.S. Food and Drug Administration, European Medicines Agency, China Food and Drug Administration, World Health Organization, and the like), and the like.

Example 46—Example Use Cases

The technologies described herein can be used in any of a wide variety of scenarios implemented on genomic information processing environments and platforms. For example, the technologies can support primary analysis, secondary analysis, and tertiary analysis workflows within or across collaborating parties. In addition to intra-analysis collaboration, cross-analysis collaboration can also be supported whereby a feedback loop of tertiary analysis results can be provided back to a party that performed secondary analysis for re-computation of the secondary analysis based on the tertiary analysis results. The technologies described herein can also be used to enforce research use only restrictions or to limit use for diagnostic purposes for approved clinical uses. Further, the technologies can be implemented to ensure compliance with privacy and/or health data residency requirements (e.g., U.S. Health Insurance Portability and Accountability Act, European General Data Protection Regulation, California Consumer Privacy Act, and the like).

Collaboration and sharing can be facilitated by policy-based access control for genomic digital data in any of a variety of workflows supporting the above as described herein. For example, tenants can collaborate on a workflow, results of a workflow can be passed from one tenant to another, and the like.

Example 47—Example Use Cases: Primary, Secondary, and Tertiary Analyses

Sequencing generates large volumes of genomic digital data, and the analysis process associated with such data can be complex. A variety of analytical tools can be used to reveal meaningful information in the data in a timely manner. The technologies described herein can enable collaboration during use of the analytical tools and related workflows as well as providing the results of one workflow from one tenant to another. One way of describing the genomic digital data analysis process divides the analysis process into three main phases: primary, secondary, and tertiary data analysis. Some actions can be performed automatically on a sequencing instrument, while others occur after sequencing is completed.

Primary data analysis can include analysis performed during cycles of sequencing chemistry and imaging, which provides base calls and associated quality scores representing the primary structure of nucleotide strands. In one example, the output of primary data analysis are BCL base call files indicating the base calls of clusters of nucleotide strands. In practice, such analysis can be performed automatically on sequencing systems. The results of primary analysis can take the form of genomic digital data embodied in files and uploaded to the cloud for further processing during secondary analysis. Collaboration and sharing can be facilitated by policy-based access control for such genomic digital data as described herein. For example, one tenant can perform primary analysis and provide access to the results to one or more tenants for secondary analysis.

Secondary analysis can take the results of primary analysis, which represent base calls of non-aligned nucleotide fragments, and provide a determination of full sequence or sequence range (e.g., a gene) by analysis and alignment of base calls of nucleotide fragments for a sample, from which genetic variants can be determined. For example, the output of secondary analysis can be in the form of FASTQ files that include sequence information and a quality score. Such analysis typically involves aligning and assembly of the nucleotide fragments. Given the full sequence or a sequence range, variants can be determined. Sequence alignment, variant calling, data visualization, RNA sequencing experiments, gene fusion detection, total RNA expression profiling, and determination of methylated bases can also be performed. Collaboration and sharing of genomic data during secondary analysis can be facilitated by policy-based access control for genomic digital data as described herein. For example, one tenant can perform secondary analysis and provide access to the results to one or more tenants for tertiary analysis.

Tertiary data analysis can include using any of a wide variety of biological data mining and interpretation tools on sequence data to convert data into knowledge. For example, variant interpretation and diagnosis can be performed on results of secondary analysis. Collaboration and sharing of genomic data during tertiary analysis can be facilitated by policy-based access control for genomic digital data as described herein. For example, tertiary data analysis can include a recommendation on whether the genomic data indicates that a patient will respond to a certain medical therapy (e.g., medicine, radiation, or the like).

Example 48—Example Use Cases: Intra-Analysis Collaboration

In any of the examples herein, the policy-based access control technologies can be used for intra-analysis collaboration, where more than one party (e.g., tenant, workgroup, or both) collaborates to perform analysis within a phase.

Example 49—Example Use Cases: Cross-Analysis Collaboration

In any of the examples herein, the policy-based access control technologies can be used for intra-analysis collaboration, where one or more parties (e.g., tenant, workgroup, or both) perform analysis that is then provided to one or more other parties to perform subsequent analysis in a different phase.

In such a case, a feedback loop of tertiary analysis results can be provided back to the party that performed the secondary analysis for revisions to re-running of the secondary analysis. The secondary analysis results can then be updated so that the tertiary analysis is revised or re-run (e.g., by the same or one or more other parties).

Example 50—Example Use Cases: Government Agency Approved Instruments and Tests

In any of the examples here, the policy-based access control technologies can be used to implement diagnostic processing across tenants for government-agency-approved diagnostic instruments and/or tests. For example, FDA approved instruments and/or tests can be conducted in scenarios where multiple tenants are involved and share data as part of a test.

Example 51—Example Use Cases: Research Processing

Access control as described herein can enforce research use only processing. For example, research use only can be conducted by tenants or workgroups within tenants collaborating across institutional and geographical boundaries in a genomic digital data sharing scenario while preserving security of data. For example, access to individual patient identifiers can be restricted so that processing of data cannot be correlated to a specific individual.

Example 52—Example Use Cases: Privacy and Data Residency

Further, access control can be implemented to ensure compliance with privacy and/or health data residency (e.g., geographical location) requirements. For example, in a research scenario, individual health data with directly identifying information can be blocked or restricted while aggregated health data sets with identifying information can be published or pushed to a third-party provider or other tenant for analysis.

In a diagnostic scenario, individual health data with directly identifying information can be permitted.

For example, an access token can be used to ensure other parties (third-party analysis providers) no longer have access to the shared data when the token expires or is revoked. Revocation can be performed due to conclusion of processing or by patient instructions.

For example, an access token can be used to ensure that data resides in a certain geographic location or region.

Example 53—Example Advantages

The policy-based sharing technologies can result in a number of advantages. For example, the ease with which sharing can be accomplished in a policy-based sharing environment can generally encourage sharing between tenants. Due to the late-binding nature of the role identifiers, it is not necessary to store a comprehensive mapping of users or tenants to roles. Instead, roles can be bound at execution time. Thus, the overall storage requirements for security data are reduced.

Similarly, the flexibility of policy-based role assignment allows incorporation of new criteria without having to redesign the platform or complicate the administration by the tenant.

Binding roles at execution time also provides more accurate role assignment. For example, a change in status or service level of a tenant can be immediately reflected rather than after some period of time in which pre-mapped roles are re-assigned.

Another advantage is that executable workflows can be shared along with the underlying data on which such workflows are executed. Thus, a tenant can share underlying data, execute a shared workflow on such underlying data, and receive analysis results. The workflow can further invoke external service providers, leading to a comprehensive collaboration scenario that is not possible without such technologies.

The trust relationships can be enforced via signed tokens as described herein. Thus, the security of the underlying data can be assured, enabling tenant-to-tenant sharing while preserving security of the underlying data. Auditing of access can also be achieved, and audit logs can be used for testing, security, or compliance purposes.

Software testing can also be more easily achieved by easily setting up a test tenant and sharing data with the test tenant, providing proof-of-concept and quality assurance testing for sharing scenarios that can then be extended to actual tenants outside of testing scenarios.

Example 54—Example Computing Systems

Figure 23:
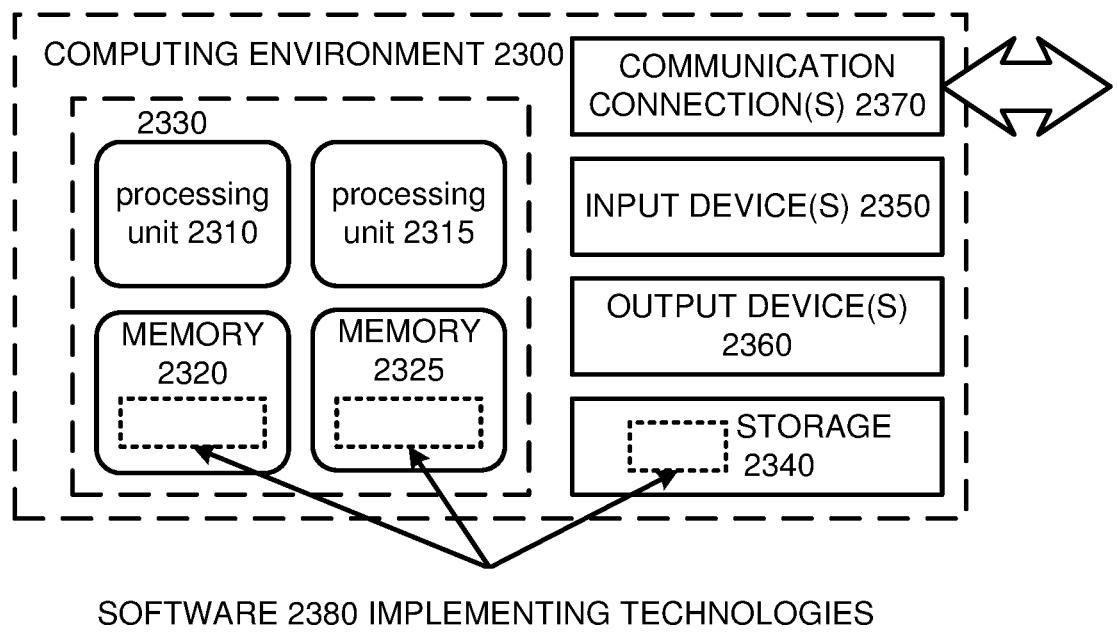
FIG. 23 is a block diagram of an example computing system in which described embodiments can be implemented.

FIG. 23 depicts an example of a suitable computing system 2300 in which digital aspects of the described innovations can be implemented. The computing system 2300 is not intended to suggest any limitation as to scope of use or functionality of the present disclosure, as the innovations can be implemented in diverse computing systems.

With reference to FIG. 23, the computing system 2300 includes one or more processing units 2310, 2315 and memory 2320, 2325. In FIG. 23, this basic configuration 2330 is included within a dashed line. The one or more processing units execute computer-executable instructions, such as for implementing the features described in the examples herein. The one or more processing units 2310, 2315 can be any combination or central processing units (CPUs), graphical processing units (CPUs), single core processors, multi-core processors, application-specific integrated circuits (ASICs), programmable circuits such as Field Programmable Gate Arrays (FPGA), and the like. One or more of the processing unit(s) 2310, 2315 may be implemented in software (e.g., ultimately executed on hardware) and/or firmware in addition to hardware implementations.

In a multi-processing system, multiple processing units execute computer-executable instructions to increase processing power. The tangible memory 2320, 2325 can be volatile memory (e.g., registers, cache, RAM), non-volatile memory (e.g., ROM, EEPROM, flash memory, etc.), or some combination of the two, accessible by the processing unit(s) 2310, 2315. The memory 2320, 2325 stores software 2380 implementing one or more innovations described herein, in the form of computer-executable instructions suitable for execution by the processing unit(s) 2310, 2315.

Functionality can also be performed, at least in part, by one or more hardware logic components. For example, Field-programmable Gate Arrays (FPGAs), Application-specific Standard Products (ASSPs), System-on-a chip systems (SOCs), Complex Programmable Logic Devices (CPLDs), and the like can be used.

A computing system 2300 can have additional features. For example, the computing system 2300 includes storage 2340, one or more input devices 2350, one or more output devices 2360, and one or more communication connections 2370, including input devices, output devices, and communication connections for interacting with a user. An interconnection mechanism (not shown) such as a bus, controller, or network interconnects the components of the computing system 2300. Typically, operating system software (not shown) provides an operating environment for other software executing in the computing system 2300, and coordinates activities of the components of the computing system 2300.

The tangible storage 2340 can be removable or non-removable, and includes magnetic disks, magnetic tapes or cassettes, CD-ROMs, DVDs, or any other medium which can be used to store information in a non-transitory way and which can be accessed within the computing system 2300. The storage 2340 stores instructions for the software 2380 implementing one or more innovations described herein.

The input device(s) 2350 can be an input device such as a keyboard, mouse, pen, or trackball, a voice input device, a scanning device, touch device (e.g., touchpad, display, or the like) or another device that provides input to the computing system 2300. The output device(s) 2360 can be a display, printer, speaker, CD-writer, or another device that provides output from the computing system 2300.

The communication connection(s) 2370 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer and should not be confused with acts performed by a human being. The actual computer operations corresponding to these terms vary depending on implementation.

Example 55—Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing system to perform the method. The technologies described herein can be implemented in a variety of programming languages.

Example 56—Example Cloud Computing Environment

Figure 24:
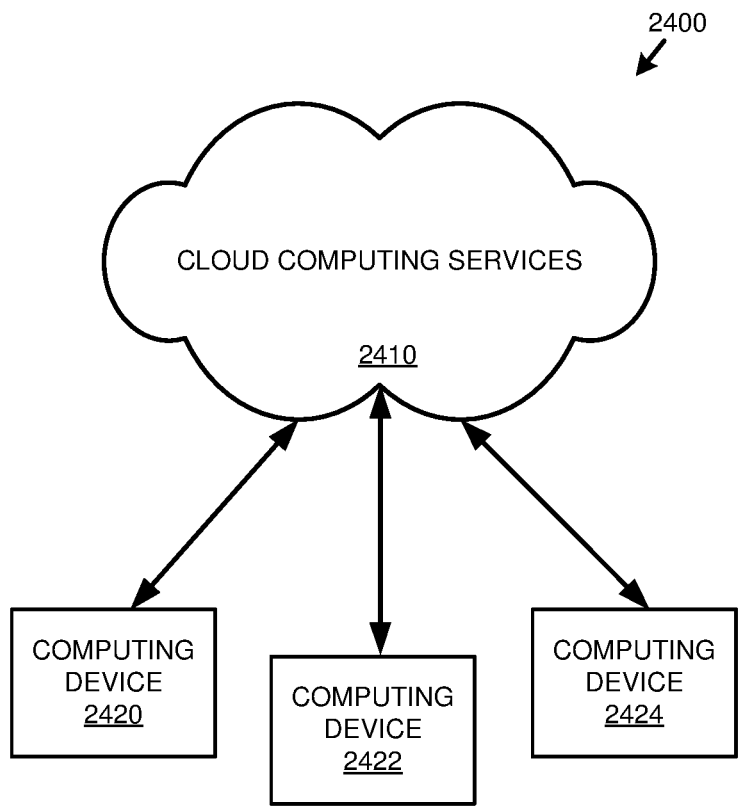
FIG. 24 is a block diagram of an example cloud computing environment that can be used in conjunction with the technologies described herein.

FIG. 24 depicts an example cloud computing environment 2400 in which the described technologies can be implemented, including, e.g., the system 100 of FIG. 1 and other systems herein. The cloud computing environment 2400 comprises cloud computing services 2410. The cloud computing services 2410 can comprise various types of cloud computing resources, such as computer servers, data storage repositories, networking resources, etc. The cloud computing services 2410 can be centrally located (e.g., provided by a data center of a business or organization) or distributed (e.g., provided by various computing resources located at different locations, such as different data centers and/or located in different cities or countries).

The cloud computing services 2410 are utilized by various types of computing devices (e.g., client computing devices), such as computing devices 2420, 2422, and 2424. For example, the computing devices (e.g., 2420, 2422, and 2424) can be computers (e.g., desktop or laptop computers), mobile devices (e.g., tablet computers or smart phones), or other types of computing devices. For example, the computing devices (e.g., 2420, 2422, and 2424) can utilize the cloud computing services 2410 to perform computing operations (e.g., data processing, data storage, and the like).

In practice, cloud-based, on-premises-based, or hybrid scenarios can be supported.

Example 57—Example Implementations

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.

Example 58—Example Embodiments

Any of the following embodiments can be implemented.

Clause 1. A method comprising:

in a computing system comprising a plurality of tenants seeking access to genomic digital data resources provided by one or more genomic data services in a software-as-a-service platform that orchestrates access to the genomic digital data resources via policy-based access control, receiving a policy-based access control definition for a first of the tenants for a given genomic digital data resource;

receiving a request for access to the given genomic digital data resource from a second of the tenants seeking access to the given genomic digital data resource; and for the second of the tenants, granting access to the given genomic digital data resource based on the policy-based access control definition.

Clause 2. The method of Clause 1 wherein:

access to the given genomic digital data resource is controlled by a role identifier linked to the policy-based access control definition; and the method further comprises:

responsive to the request for access, providing the role identifier specified in the policy-based access control definition for the request for access.

Clause 3. The method of Clause 2 wherein:

assigning the role identifier comprises late binding of the role identifier to a user identifier or tenant identifier of the request for access.

Clause 4. The method of any one of Clauses 2-3 further comprising:

responsive to the request for access, generating a signed access token containing the role identifier;

wherein access is granted based on presence of the role identifier in the signed access token.

Clause 5. The method of Clause 4 wherein:

access is further granted based on validation of the signed access token.

Clause 6. The method of any one of Clauses 4-5 further comprising:

publishing a signed grant token comprising the role identifier and a tenant identifier of a role administrator of the role identifier;

wherein access is further granted based on whether the tenant identifier of the signed grant token has sufficient rights to grant resources specified for the role identifier.

Clause 7. The method of any one of Clauses 1-6, wherein the first of the tenants comprises a proxy tenant representing an external service provider for which policy-based sharing is implemented.

Clause 8. The method of any one of Clauses 1-7 wherein the policy-based access control definition comprises a reference to a smart contract.

Clause 9. The method of any one of Clauses 1-8 wherein the policy-based access control definition comprises a reference to a service level of the second of the tenants, and access is granted according to the service level of the second of the tenants determined at a time of the request.

Clause 10. The method of any one of Clauses 1-9 wherein the policy-based access control definition specifies one or more access control statements comprising a filter attribute and a filter parameter.

Clause 11. The method of Clause 10 wherein the filter parameter specifies a wildcard for the filter attribute.

Clause 12. The method of any one of Clauses 10-11 wherein the filter attribute comprises an application.

Clause 13. The method of any one of Clauses 10-12 wherein the filter attribute comprises an application role identifier.

Clause 14. The method of any one of Clauses 1-13 wherein the policy-based access control definition supports access control statements that specify an access outcome, a tenant identifier, and one or more conditions under which access is granted.

Clause 15. The method of any one of Clauses 1-14 wherein the policy-based access control definition supports public access, private access, and application-based access.

Clause 16. The method of any one of Clauses 1-15 wherein the policy-based access control definition comprises a parameter evaluated at execution time.

Clause 17. The method of Clause 16 wherein:

the parameter of the policy-based access control definition comprises an application identifier parameter; and granting access comprises comparing the application identifier parameter of the policy-based access control definition with an application identifier specified by the second of the tenants seeking access to the genomic digital data resources.

Clause 18. The method of any one of Clauses 16-17 wherein:

the parameter of the policy-based access control definition comprises a tenant identifier parameter; and granting access comprises comparing the tenant identifier parameter of the access control definition with a tenant identifier of the second tenant seeking access to the genomic digital data resources.

Clause 19. A multi-tenant, cloud-based system comprising:
  one or more processors;
  memory coupled to the one or more processors;
  a policy store comprising a policy-based access control definition received for a first tenant and comprising a role identifier;
  a genomic digital data resource linked to the role identifier;
  wherein the memory comprises computer-executable instructions causing the one or more processors to perform operations comprising:
  receiving a request for access to the genomic digital data resource from a second tenant seeking access to the genomic digital data resource; and
  for the second tenant, granting access to the genomic digital data resource according to the policy-based access control definition evaluated at a time of the request for access.

Clause 20. One or more computer-readable media comprising:
  computer-executable instructions capable of causing a computing system to receive a publishing request for a first tenant to provide access to genomic digital data, wherein access to the genomic digital data is controlled by a role identifier linked to a policy document, wherein the policy document comprises one or more conditions;
  computer-executable instructions capable of causing a computing system to receive a request from a second tenant for access to the genomic digital data to which access is controlled by the role identifier linked to the policy document, wherein the request comprises one or more attributes;
  computer-executable instructions capable of causing the computing system to access the policy document responsive to the request from the second tenant for access; and
  computer-executable instructions capable of causing the computing system to generate an access token based on the one or more attributes and the one or more conditions, wherein the role identifier is included in the access token responsive to determining that the one or more conditions are fulfilled by the one or more attributes. and the access token authorizes access to the genomic digital data via the role identifier.

Clause 21 One or more computer-readable media comprising computer-executable instructions that when executed by a computing system, cause the computing system to perform the method of any one of Clauses 1-18.

Example 59—Example Alternatives

The technologies from any example can be combined with the technologies described in any one or more of the other examples. In view of the many possible embodiments to which the principles of the disclosed technology can be applied, it should be recognized that the illustrated embodiments are examples of the disclosed technology and should not be taken as a limitation on the scope of the disclosed technology. Rather, the scope of the disclosed technology includes what is covered by the scope and spirit of the following claims.

What is claimed is:

1. A method comprising:
  in a computing system comprising a plurality of tenants seeking access to genomic digital data resources provided by one or more genomic data services in a software-as-a-service platform that orchestrates access to the genomic digital data resources via policy-based access control, receiving a policy-based access control definition for a first of the tenants for a given genomic digital data resource, wherein the genomic digital data resource comprises genomic data originating from a sequencing instrument, and the policy-based access control definition supports access control statements that specify one or more conditions under which access is granted;
  receiving a request for access to the given genomic digital data resource from a second of the tenants seeking access to the given genomic digital data resource, wherein the request comprises one or more attributes;
  accessing the policy-based access control definition responsive to the request from the second of the tenants;
  generating an access token based on the one or more attributes and the one or more conditions;
  adding a role identifier of the policy-based access control definition into the access token; and
  granting the second of the tenants to access to the given genomic digital data resource based on the policy-based access control definition.

2. The method of claim 1 wherein:
  access to the given genomic digital data resource is controlled by a role identifier linked to the policy-based access control definition; and
  the method further comprises:
  responsive to the request for access, providing the role identifier specified in the policy-based access control definition for the request for access.

3. The method of claim 2 wherein:
  assigning the role identifier comprises late binding of the role identifier to a user identifier or tenant identifier of the request for access.

4. The method of claim 2 further comprising:
  responsive to the request for access, generating a signed access token containing the role identifier;
  wherein access is granted based on presence of the role identifier in the signed access token.

5. The method of claim 4 wherein:
  access is further granted based on validation of the signed access token.

6. The method of claim 4 further comprising:
  publishing a signed grant token comprising the role identifier and a tenant identifier of a role administrator of the role identifier;
  wherein access is further granted based on whether the tenant identifier of the signed grant token has sufficient rights to grant resources specified for the role identifier.

7. The method of claim 1, wherein the first of the tenants comprises a proxy tenant representing an external service provider for which policy-based sharing is implemented.

8. The method of claim 1 wherein the policy-based access control definition comprises a reference to a smart contract.

9. The method of claim 1 wherein the policy-based access control definition comprises a reference to a service level of the second of the tenants, and access is granted according to the service level of the second of the tenants determined at a time of the request.

10. The method of claim 1 wherein the policy-based access control definition specifies one or more access control statements comprising a filter attribute and a filter parameter.

11. The method of claim 10 wherein the filter parameter specifies a wildcard for the filter attribute.

12. The method of claim 10 wherein the filter attribute comprises an application.

13. The method of claim 10 wherein the filter attribute comprises an application role identifier.

14. The method of claim 1 wherein the policy-based access control definition supports access control statements that specify an access outcome and a tenant identifier.

15. The method of claim 1 wherein the policy-based access control definition supports public access, private access, and application-based access.

16. The method of claim 1 wherein the policy-based access control definition comprises a parameter evaluated at execution time.

17. The method of claim 16 wherein:
the parameter of the policy-based access control definition comprises an application identifier parameter; and
granting access comprises comparing the application identifier parameter of the policy-based access control definition with an application identifier specified by the second of the tenants seeking access to the genomic digital data resources.

18. The method of claim 16 wherein:
the parameter of the policy-based access control definition comprises a tenant identifier parameter; and
granting access comprises comparing the tenant identifier parameter of the access control definition with a tenant identifier of the second tenant seeking access to the genomic digital data resources.

19. A multi-tenant, cloud-based system comprising:
one or more processors;
memory coupled to the one or more processors;
a policy store comprising a policy-based access control definition received for a first tenant, a role identifier, and one or more conditions;
a genomic digital data resource linked to the role identifier, wherein the genomic digital data resource comprises genomic data originating from a sequencing instrument;
wherein the memory comprises computer-executable instructions causing the one or more processors to perform operations comprising:
receiving a request for access to the genomic digital data resource from a second tenant seeking access to the genomic digital data resource, wherein the request comprises one or more attributes;
accessing the policy-based control definition responsive to the request from the second tenant for access;
generating an access token based on the one or more attributes and the one or more conditions;
adding the role identifier into the access token responsive to determining that the one or more conditions are fulfilled by the one or more attributes;
granting the second tenant to access to the genomic digital data resource according to the policy-based control definition evaluated at a time of the request for access.

20. One or more non-transitory computer-readable media storing computer-executable instructions that, when executed by a processor, performs operations of:
receiving a publishing request for a first tenant to provide access to genomic digital data, wherein access to the genomic digital data is controlled by a role identifier linked to a policy document, wherein the policy document comprises one or more conditions;
receiving a request from a second tenant for access to the genomic digital data to which access is controlled by the role identifier linked to the policy document, wherein the request comprises one or more attributes;
accessing the policy document responsive to the request from the second tenant for access;
generating an access token based on the one or more attributes and the one or more conditions;
adding the role identifier into the access token responsive to determining that the one or more conditions are fulfilled by the one or more attributes, wherein the access token authorizes access to the genomic digital data via the role identifier; and
granting the second tenant to access to the genomic digital data.

* * * * *